United States Patent
Wang et al.

(10) Patent No.: US 11,668,295 B2
(45) Date of Patent: Jun. 6, 2023

(54) PUMP HEAD FOR A PERISTALTIC PUMP

(71) Applicant: Avent, Inc., Alpharetta, GA (US)

(72) Inventors: Ruoya Wang, Decatur, GA (US); Michael D. Brown, Alpharetta, GA (US); Jennifer J. Barrett, Alpharetta, GA (US); Kun-Chi Wu, Johns Creek, GA (US); Claire B. Couch, Alpharetta, GA (US); Ken Driver, Brookhaven, GA (US)

(73) Assignee: Avent, Inc., Alpharetta, GA (US)

( * ) Notice: Subject to any disclaimer, the term of this patent is extended or adjusted under 35 U.S.C. 154(b) by 604 days.

(21) Appl. No.: 16/234,803

(22) Filed: Dec. 28, 2018

(65) Prior Publication Data
US 2020/0208624 A1 Jul. 2, 2020

(51) Int. Cl.
*F04B 43/09* (2006.01)
*F04B 43/12* (2006.01)
(Continued)

(52) U.S. Cl.
CPC .......... *F04B 43/1246* (2013.01); *A61B 18/14* (2013.01); *F04B 43/0081* (2013.01);
(Continued)

(58) Field of Classification Search
CPC .......... A61B 18/14; A61B 2018/00023; A61B 2018/00339; A61B 2018/00565;
(Continued)

(56) References Cited

U.S. PATENT DOCUMENTS 3,918,854 A * 11/1975 Catarious ............ F04B 43/1284
417/477.11
3,963,023 A * 6/1976 Hankinson .......... F04B 43/1276
604/19
(Continued)

FOREIGN PATENT DOCUMENTS

CN 206714820 U 12/2017
EP 2 253 345 A1 11/2010
(Continued)

OTHER PUBLICATIONS

International Search Report and Written Opinion for PCT/US2019/067431, dated Apr. 9, 2020, 16 pages.
(Continued)

*Primary Examiner* — Philip E Stimpert
*Assistant Examiner* — Dnyanesh G Kasture
(74) *Attorney, Agent, or Firm* — Meunier Carlin & Curfman LLC

(57) ABSTRACT

Pump heads for peristaltic pump assemblies are provided. For example, a pump head for a peristaltic pump comprises an occlusion bed, a rotor guide, a rotor assembly positioned between the occlusion bed and the rotor guide, and a pathway for tubing. The pathway comprises an inlet portion, an outlet portion, and a connecting portion that connects the inlet and outlet portions. The inlet portion is defined between the occlusion bed and the rotor guide, the outlet portion is defined between the occlusion bed and the rotor guide, and the connecting portion is defined between the occlusion bed and the rotor assembly. Further, the occlusion bed is movable with respect to the rotor guide and the rotor assembly. In exemplary embodiments, the pump head urges fluid flow through the tubing to supply a cooling fluid to a medical probe assembly for delivering energy to a patient's body.

18 Claims, 14 Drawing Sheets

(51) Int. Cl.
  *A61B 18/14* (2006.01)
  *F04B 43/00* (2006.01)
  *A61B 18/00* (2006.01)
(52) U.S. Cl.
  CPC .............. *F04B 43/1284* (2013.01); *A61B 2018/00023* (2013.01); *A61B 2018/00339* (2013.01); *A61B 2018/00565* (2013.01); *A61B 2018/00577* (2013.01); *A61B 2018/00589* (2013.01); *A61B 2018/00595* (2013.01); *A61B 2018/00642* (2013.01)
(58) Field of Classification Search
  CPC ........... A61B 2018/00577; A61B 2018/00589; A61B 2018/00595; A61B 2018/00642; A61M 5/44; A61M 5/14232; F04B 43/1246; F04B 43/0081; F04B 53/16; F04B 43/1253; F04B 43/1284; F04B 53/22; F04B 45/08; F04B 43/09; F04B 43/12
  USPC ...................................... 417/477.2
  See application file for complete search history.

(56) References Cited

U.S. PATENT DOCUMENTS

| | | | | |
|---|---|---|---|---|
| 3,990,444 | A * | 11/1976 | Vial | A61M 5/142 604/67 |
| 4,155,362 | A * | 5/1979 | Jess | F04B 43/1284 604/507 |
| 4,221,543 | A * | 9/1980 | Cosentino | F04B 43/1253 417/22 |
| 4,424,011 | A * | 1/1984 | O'Brien | B05C 17/0308 401/146 |
| 5,334,181 | A | 8/1994 | Rubinsky et al. | |
| 5,538,405 | A | 7/1996 | Patno et al. | |
| 5,759,017 | A * | 6/1998 | Patton | F04B 43/1253 417/477.11 |
| 5,928,177 | A * | 7/1999 | Brugger | F04B 43/1253 604/6.11 |
| 7,004,961 | B2 | 2/2006 | Wong et al. | |
| 7,344,499 | B1 | 3/2008 | Prausnitz et al. | |
| 7,513,757 | B2 * | 4/2009 | Gibson | F04B 43/1253 417/477.12 |
| 7,597,546 | B2 * | 10/2009 | Brieske | F04B 43/1253 417/477.11 |
| 7,771,420 | B2 | 8/2010 | Butty et al. | |
| 7,857,756 | B2 | 12/2010 | Warren et al. | |
| 8,361,063 | B2 | 1/2013 | Godara | |
| 9,072,540 | B2 * | 7/2015 | Jarnagin | A61M 1/80 |
| 9,474,573 | B2 * | 10/2016 | Leung | A61B 18/18 |
| 9,480,528 | B2 | 11/2016 | Turovskiy et al. | |
| 9,603,990 | B2 | 3/2017 | Woolford | |
| 9,662,169 | B2 | 5/2017 | Schultz et al. | |
| 9,956,032 | B1 | 5/2018 | Cosman et al. | |
| 2003/0199794 | A1 | 10/2003 | Sakurai et al. | |
| 2005/0096549 | A1 | 5/2005 | Gerber et al. | |
| 2005/0177210 | A1 | 8/2005 | Leung et al. | |
| 2006/0177328 | A1 | 8/2006 | Nordell et al. | |
| 2007/0027449 | A1 | 2/2007 | Godara et al. | |
| 2007/0258838 | A1 | 11/2007 | Drake et al. | |
| 2009/0129944 | A1 * | 5/2009 | Stemple | F04B 43/1284 417/53 |
| 2010/0129248 | A1 * | 5/2010 | Mou | F04B 43/1284 417/477.9 |
| 2010/0224547 | A1 * | 9/2010 | Fujii | A61M 5/14232 210/236 |
| 2011/0004161 | A1 * | 1/2011 | Ito | A61M 5/1424 604/154 |
| 2011/0054378 | A1 | 3/2011 | Fulkerson | |
| 2011/0077643 | A1 | 3/2011 | Dahla et al. | |
| 2011/0300010 | A1 | 12/2011 | Jarnagin et al. | |
| 2012/0180577 | A1 * | 7/2012 | Steere | F04B 43/12 73/863.23 |
| 2013/0030426 | A1 | 1/2013 | Gallardo et al. | |
| 2015/0204321 | A1 | 7/2015 | Schnekenburger et al. | |
| 2017/0021306 | A1 | 1/2017 | Fulkerson et al. | |

FOREIGN PATENT DOCUMENTS

| | | |
|---|---|---|
| EP | 2 997 021 A1 | 1/2016 |
| FR | 2 669 539 A1 | 5/1992 |
| WO | WO 03/000316 A1 | 1/2003 |
| WO | WO 2010/018569 A1 | 2/2010 |
| WO | WO 2017/039570 A1 | 3/2017 |

OTHER PUBLICATIONS

International Preliminary Report on Patentability received in PCT/US2019/067431 dated Jul. 8, 2021, 11 pages.

* cited by examiner

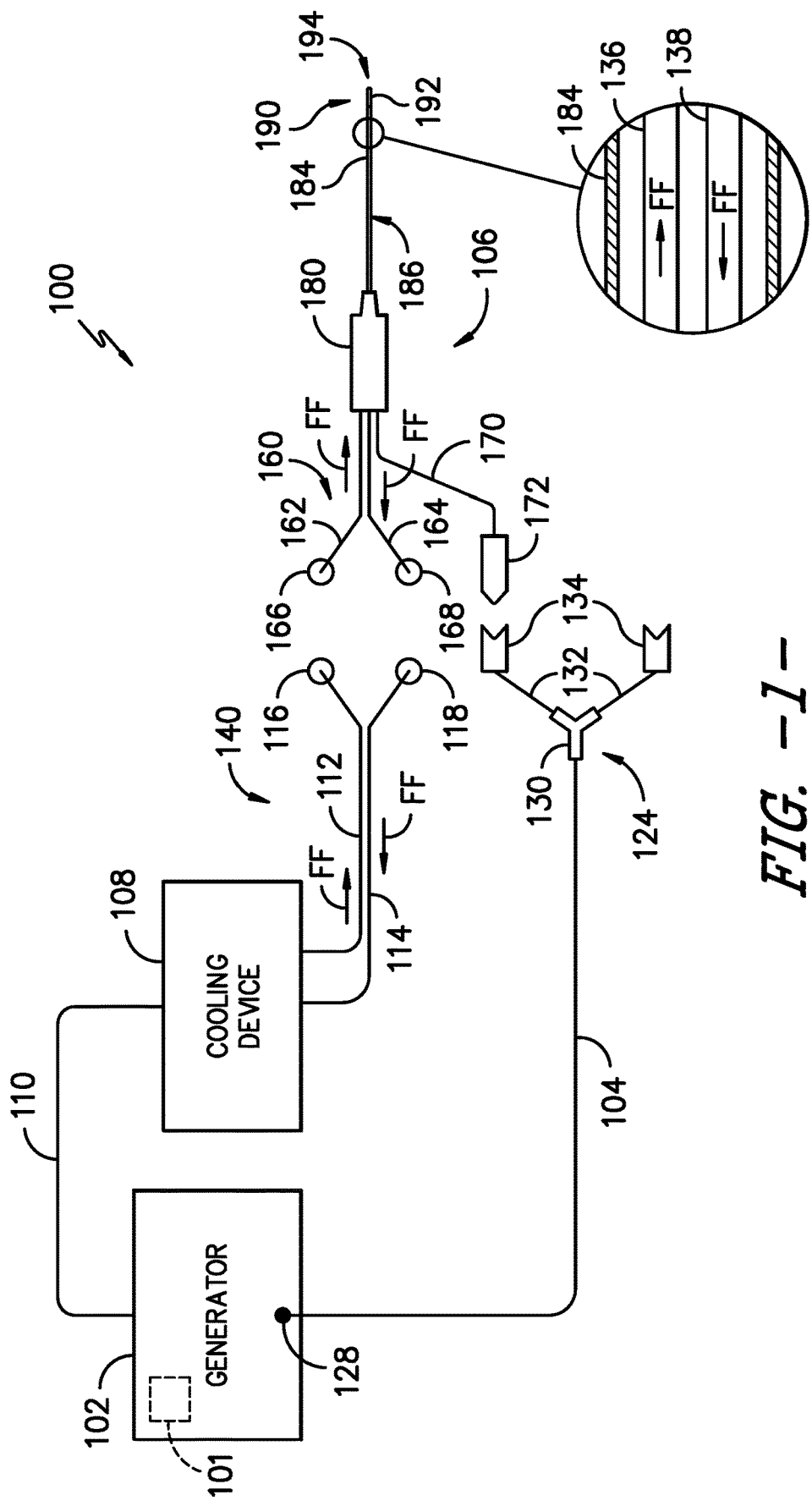
FIG. -1-

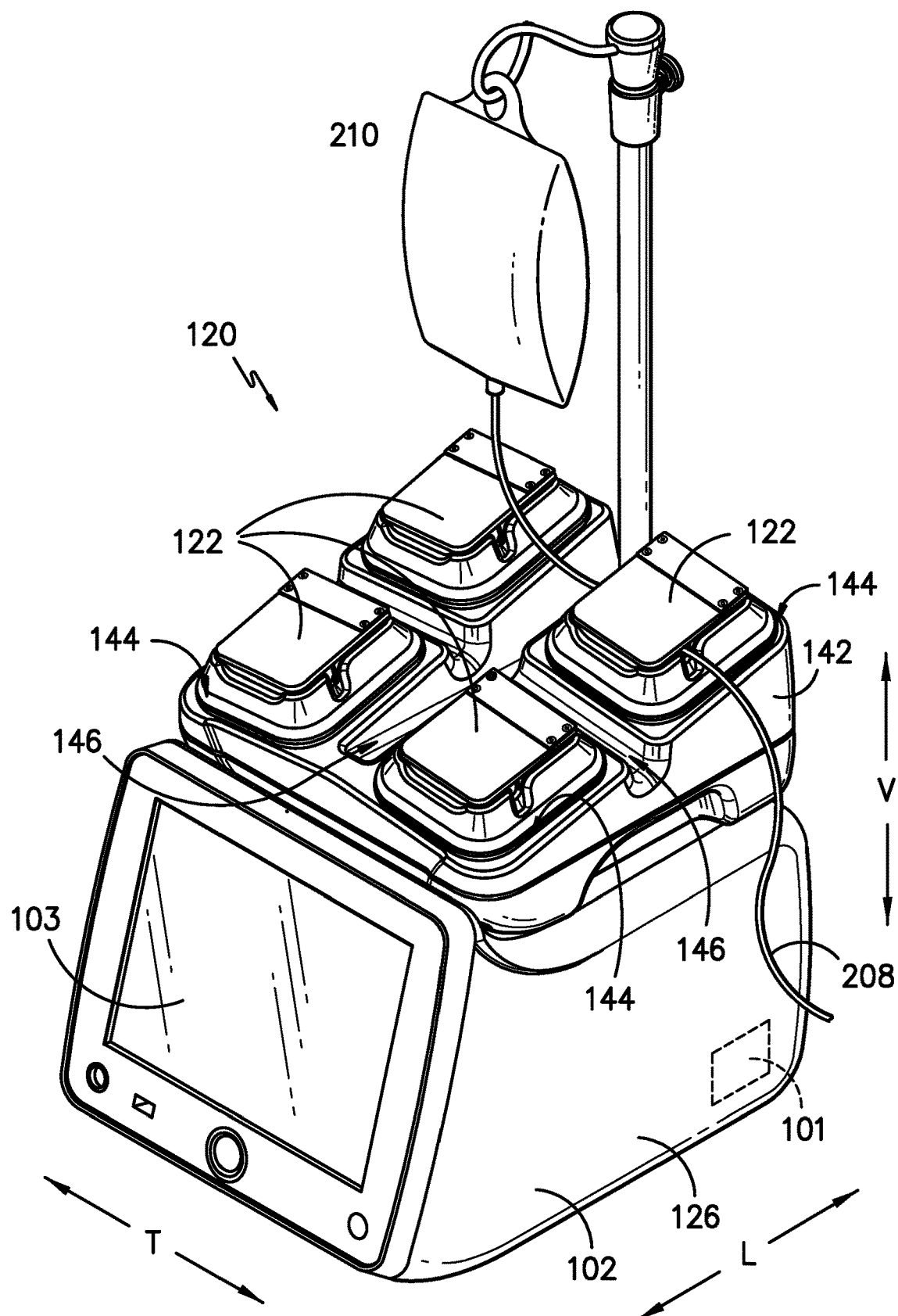
FIG. -2-

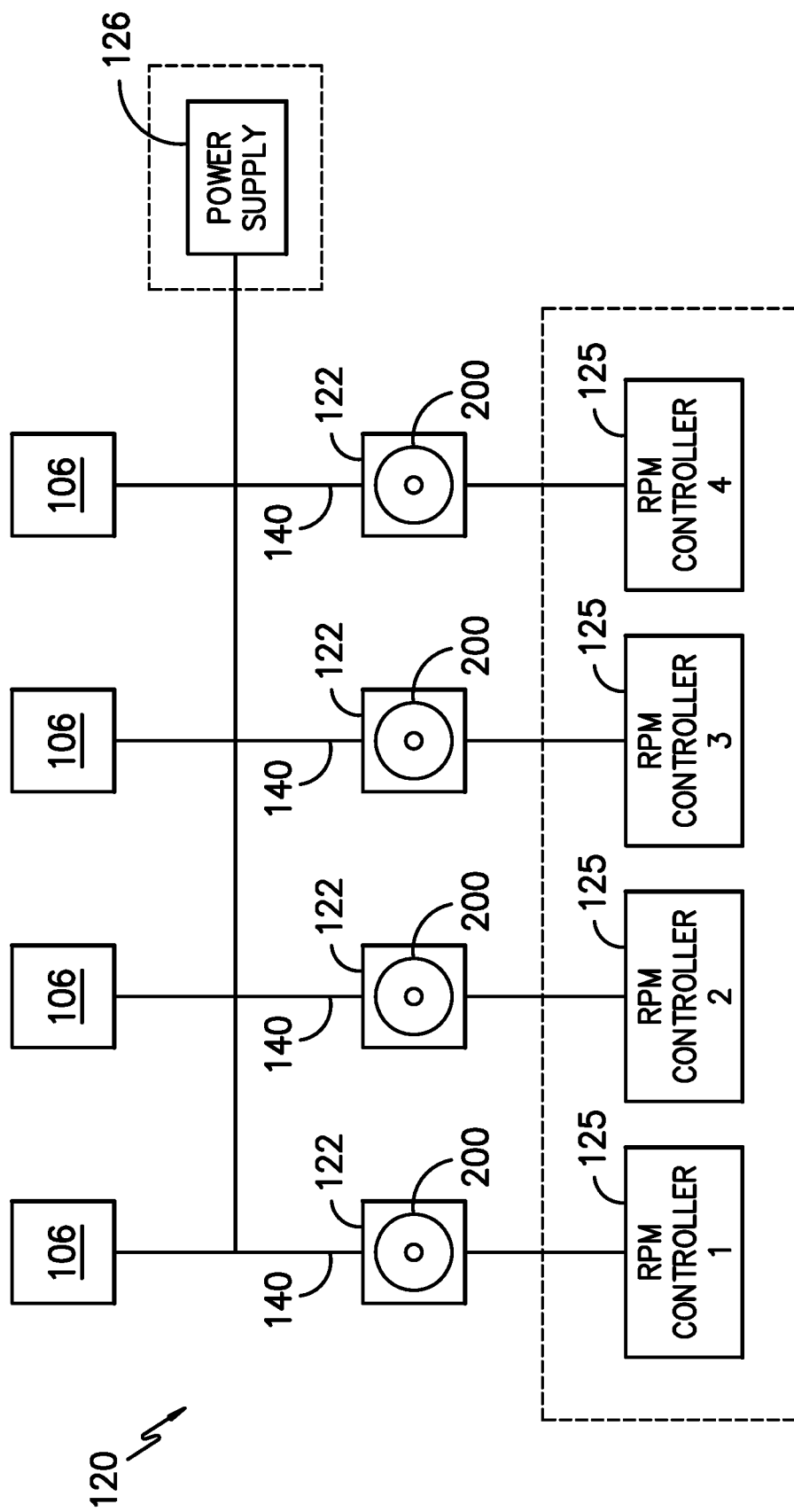
FIG. -3-

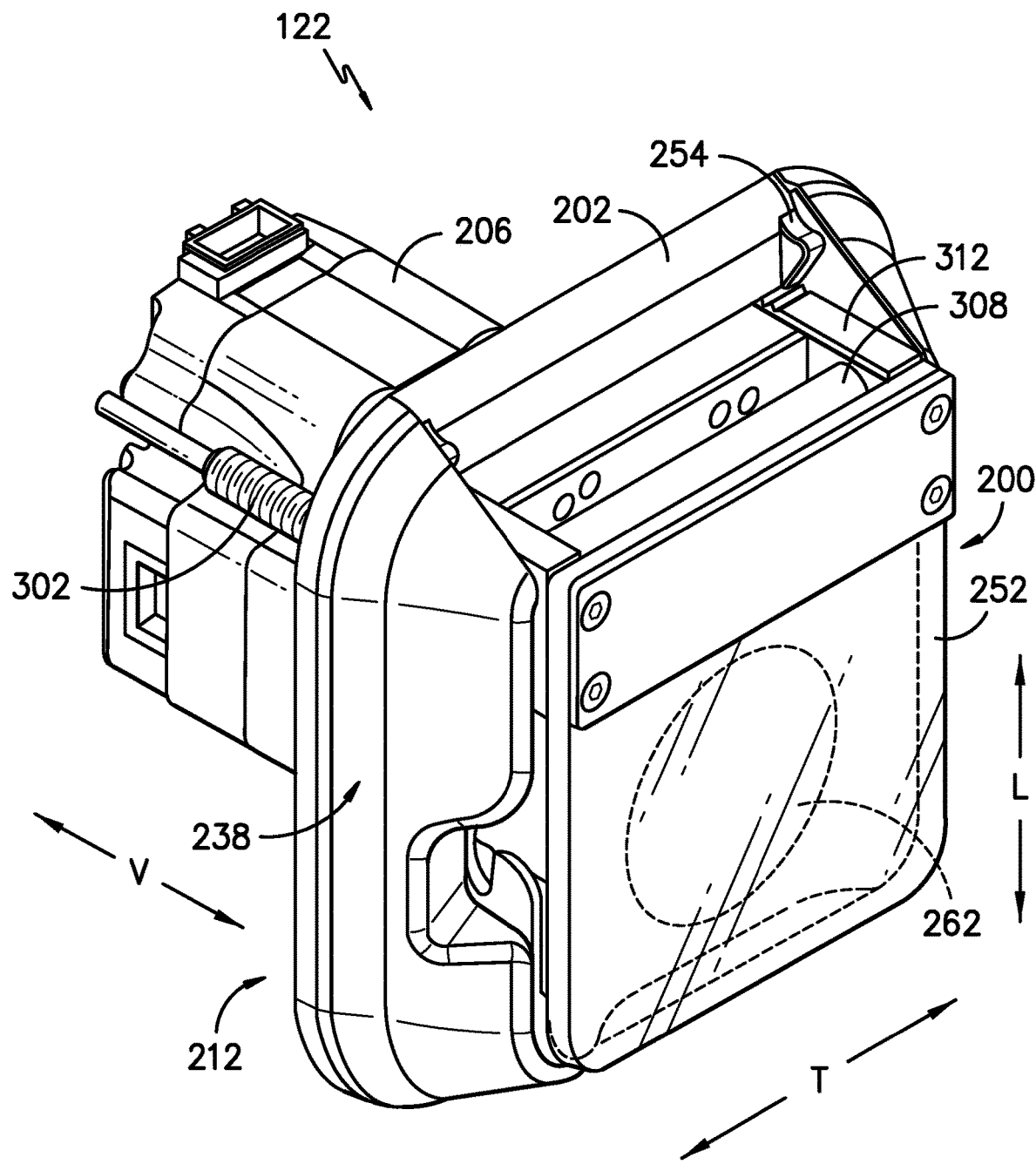
FIG. -4-

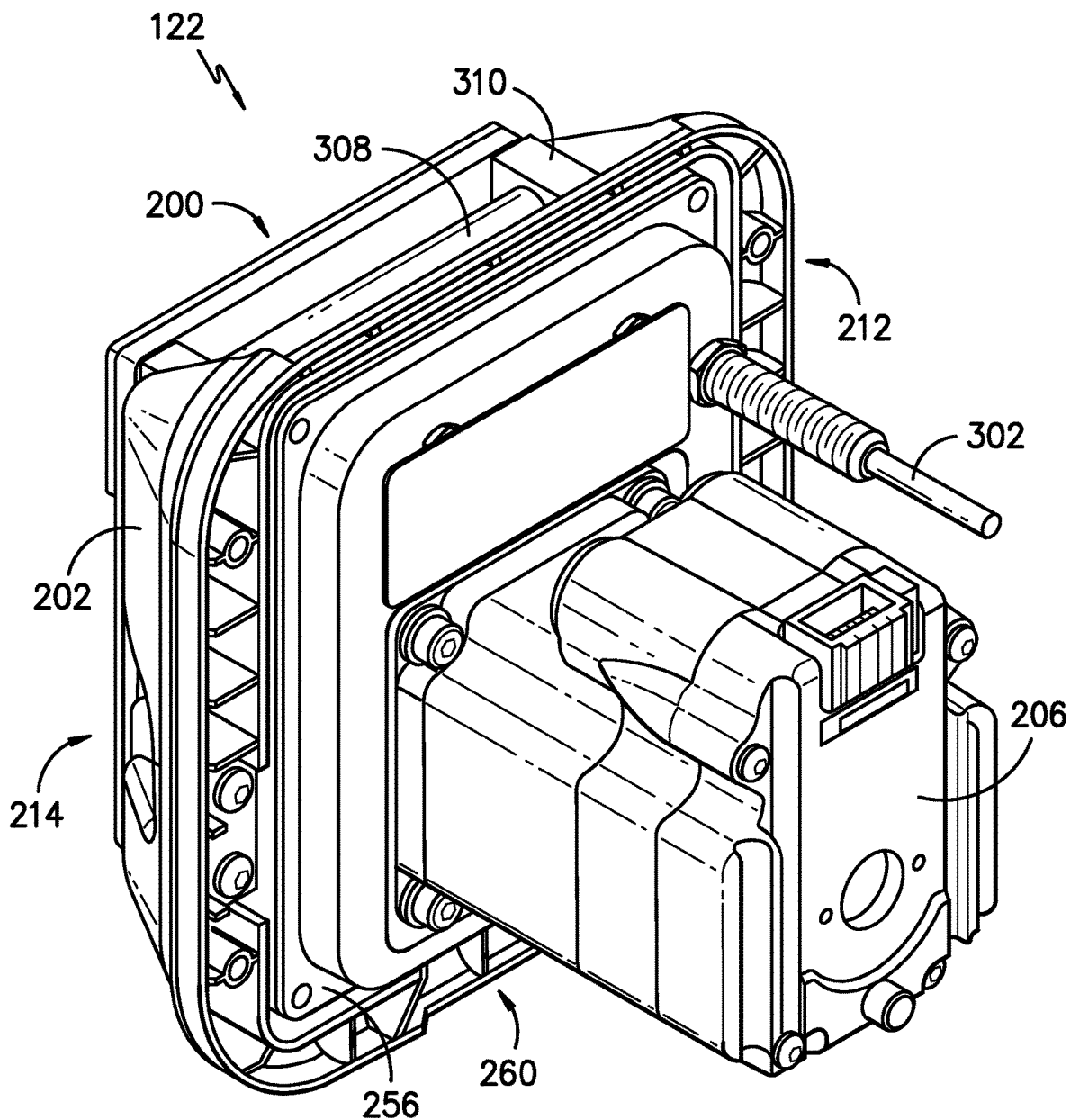
FIG. -5-

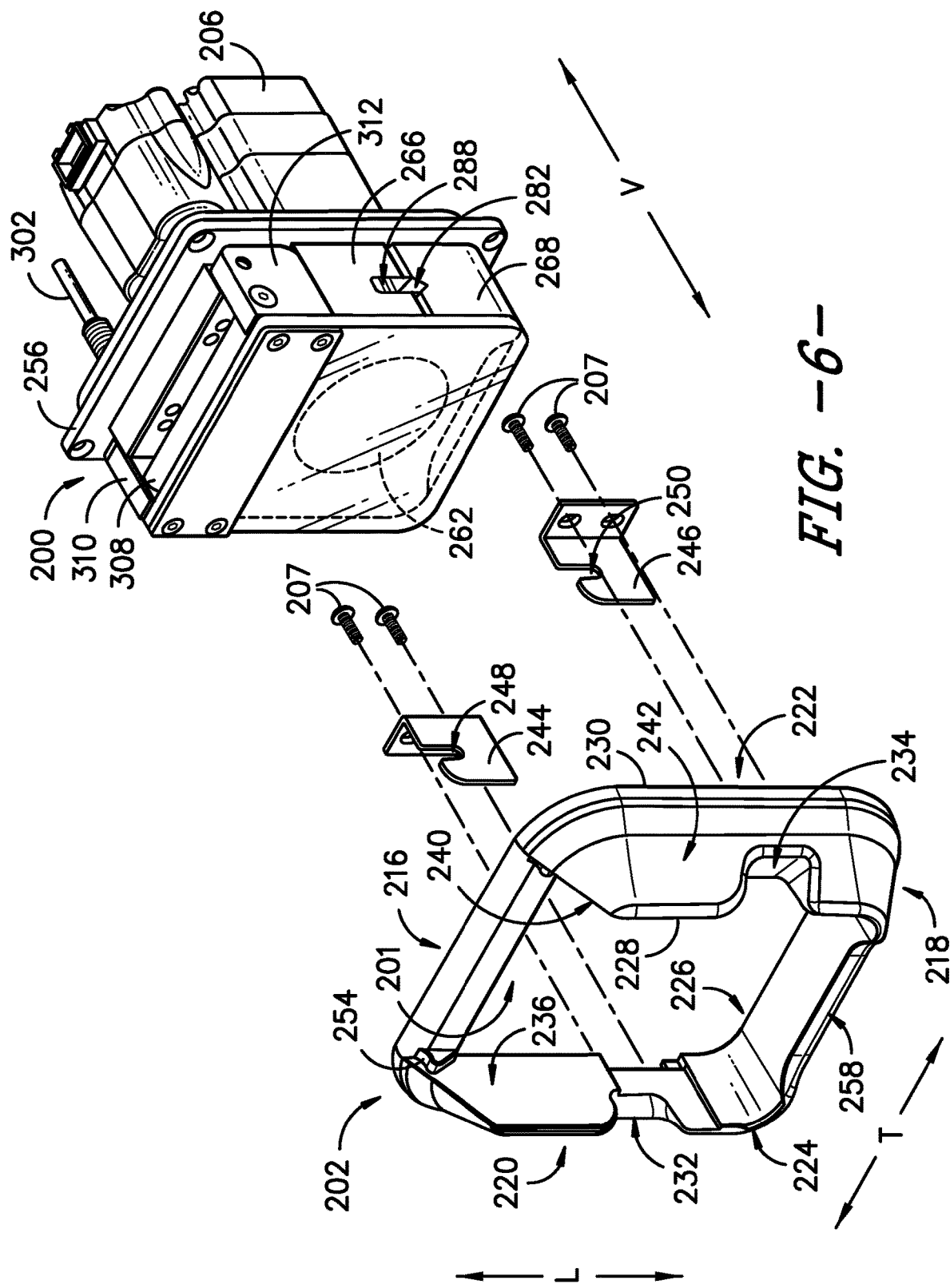
FIG. -6-

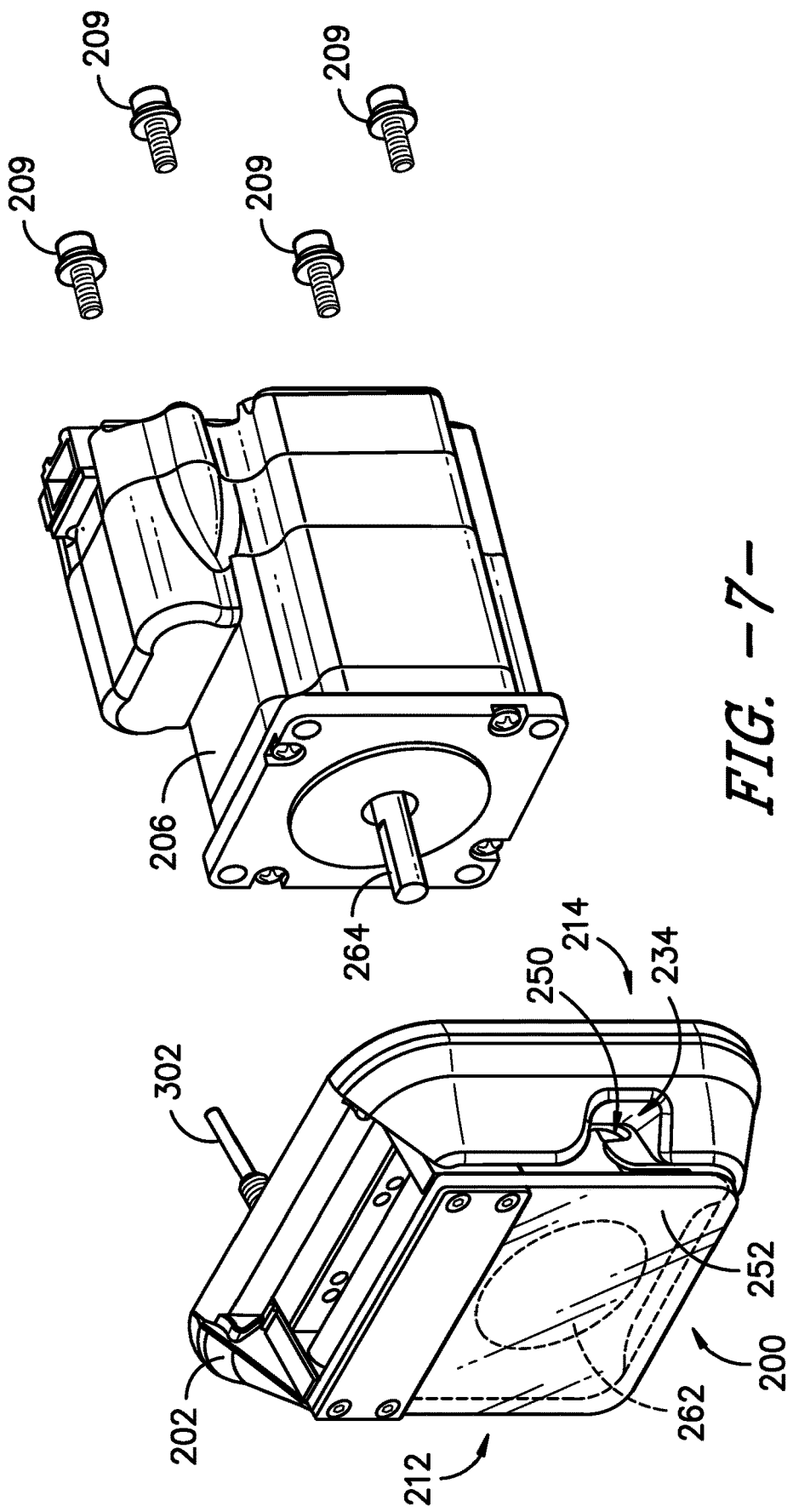

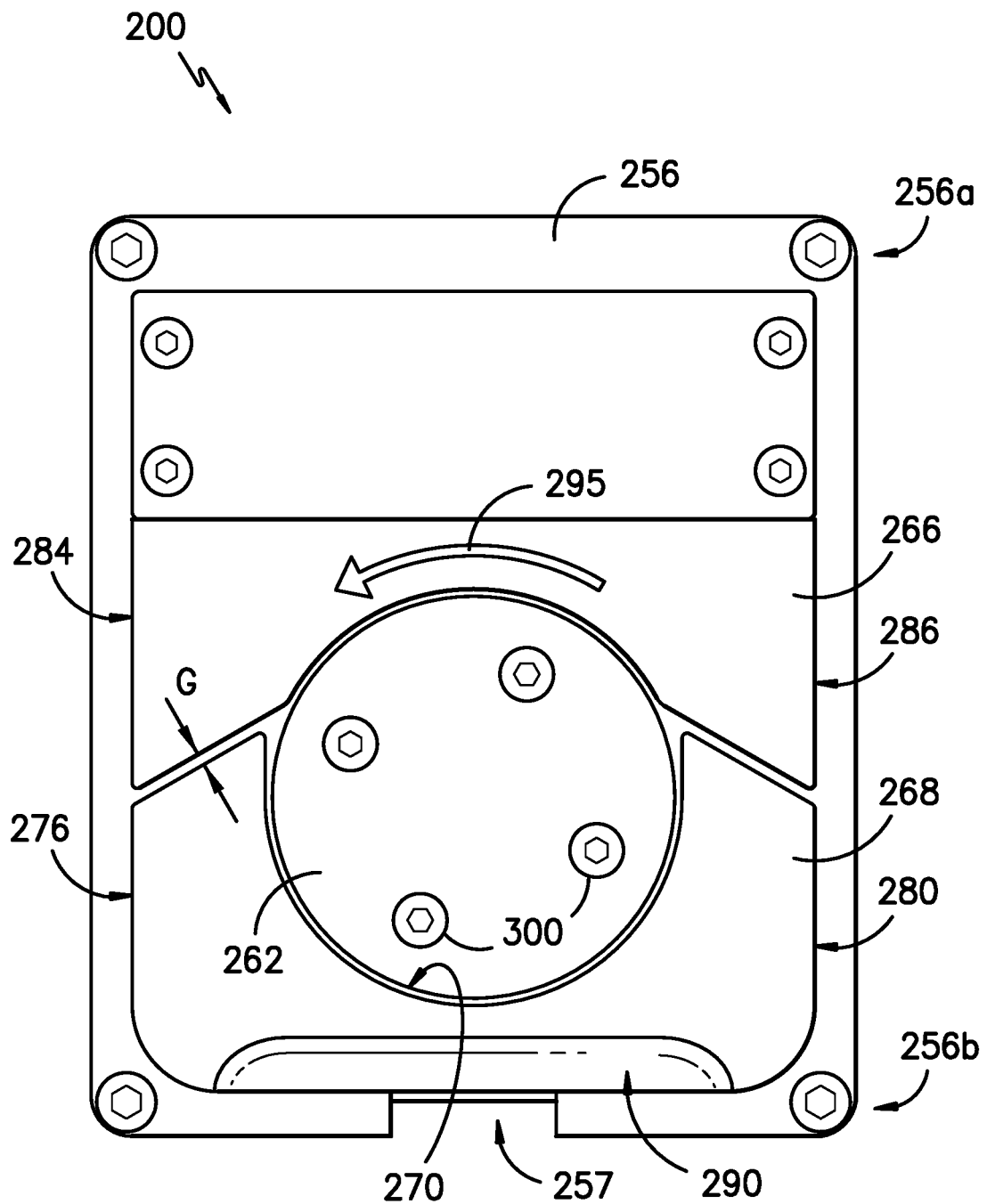
FIG. -8-

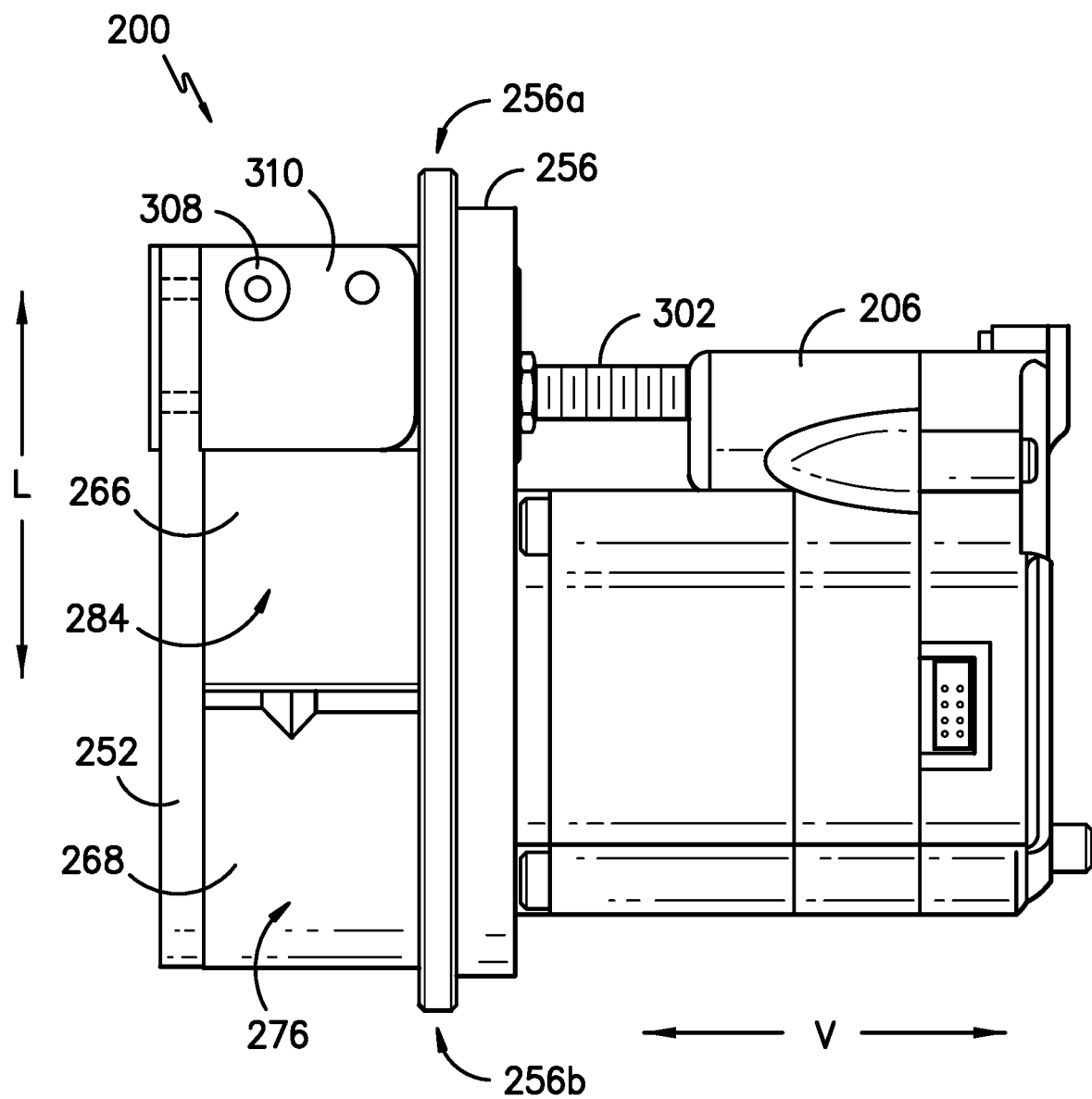
FIG. -9-

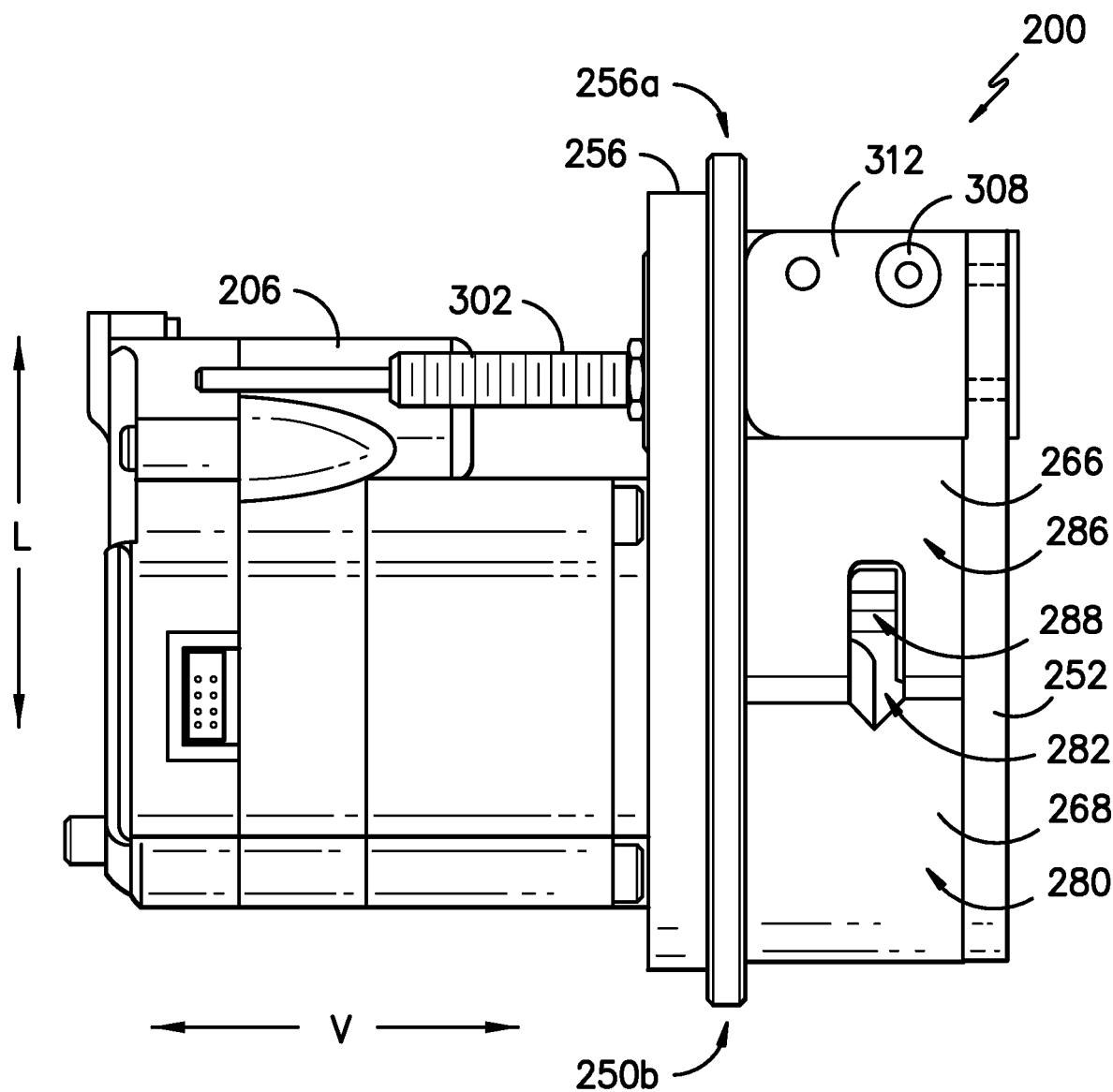
FIG. -10-

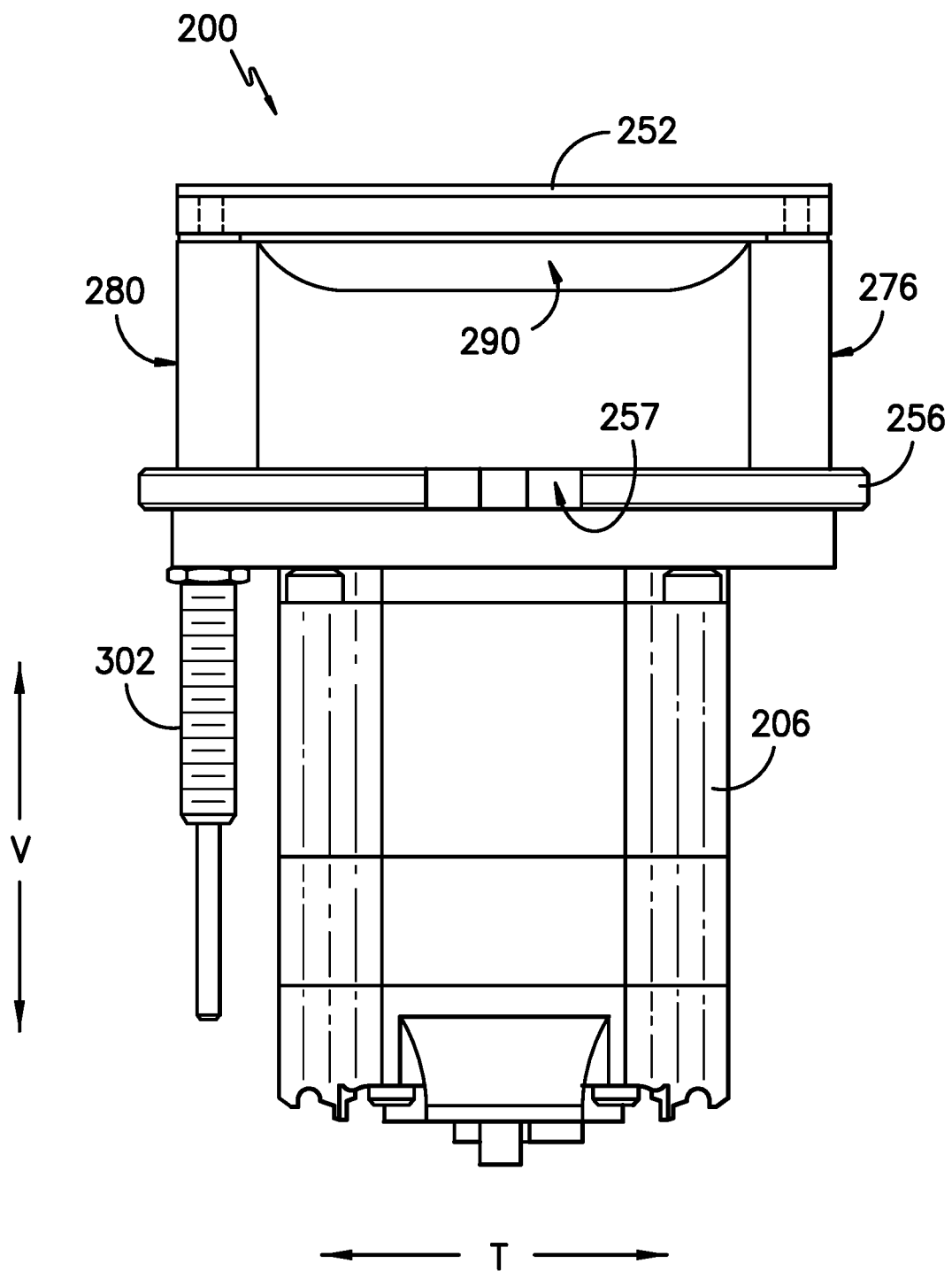
FIG. -11-

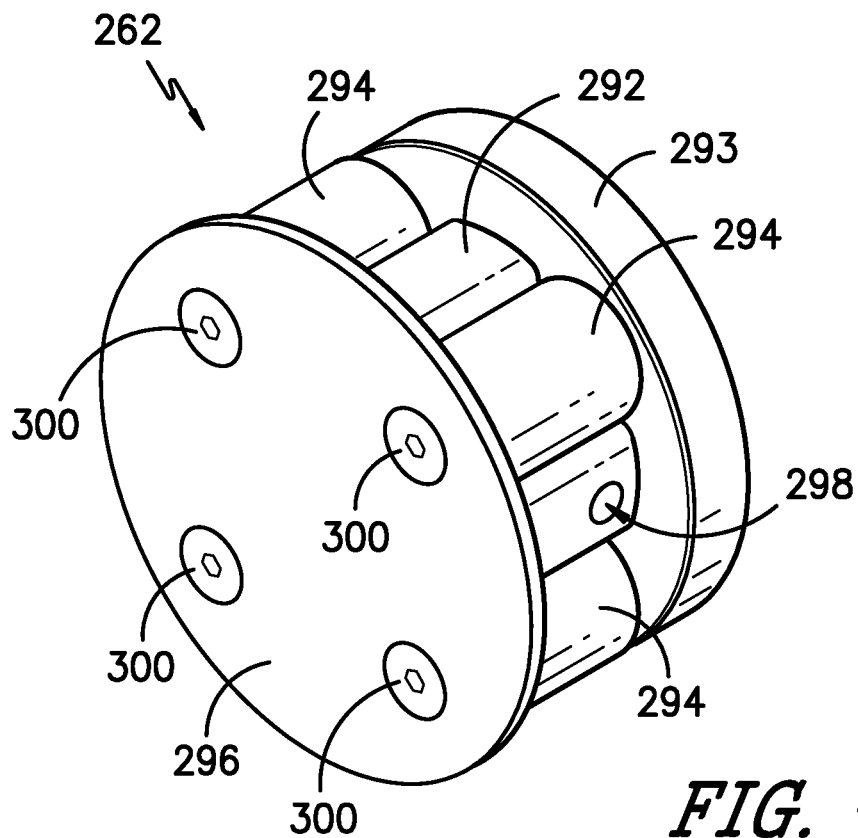
FIG. -12-
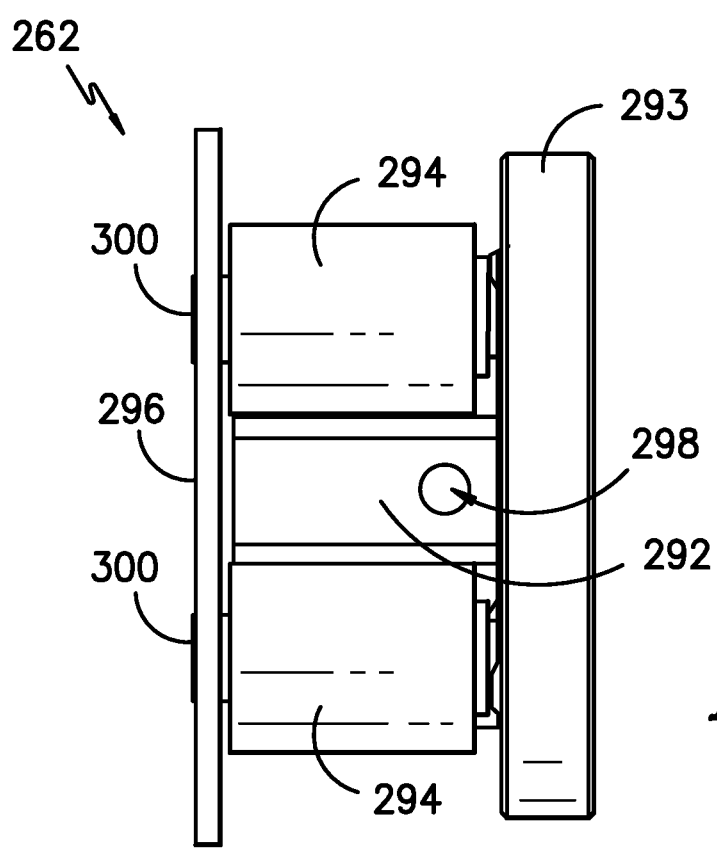
FIG. -13-

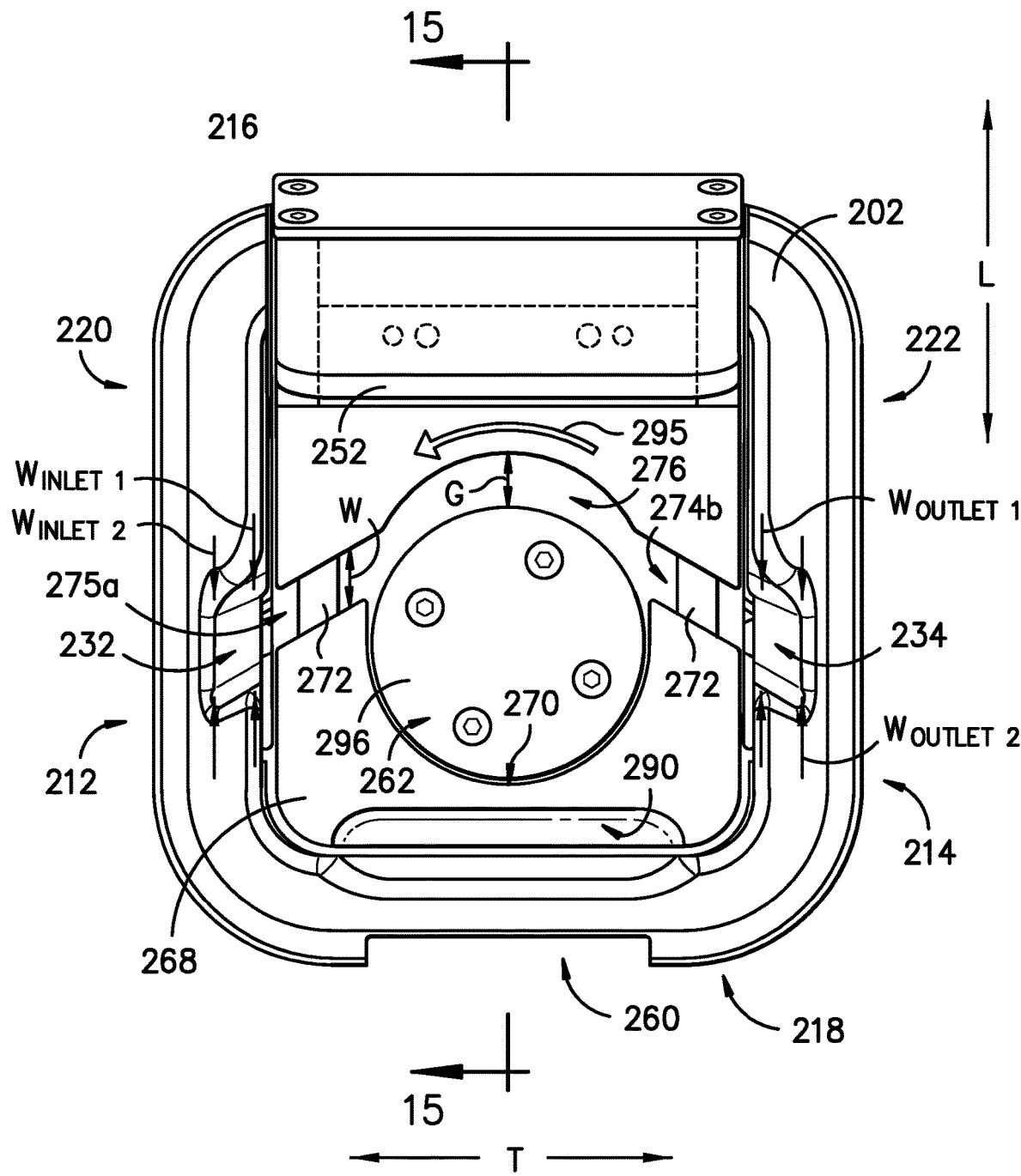
FIG. -14-

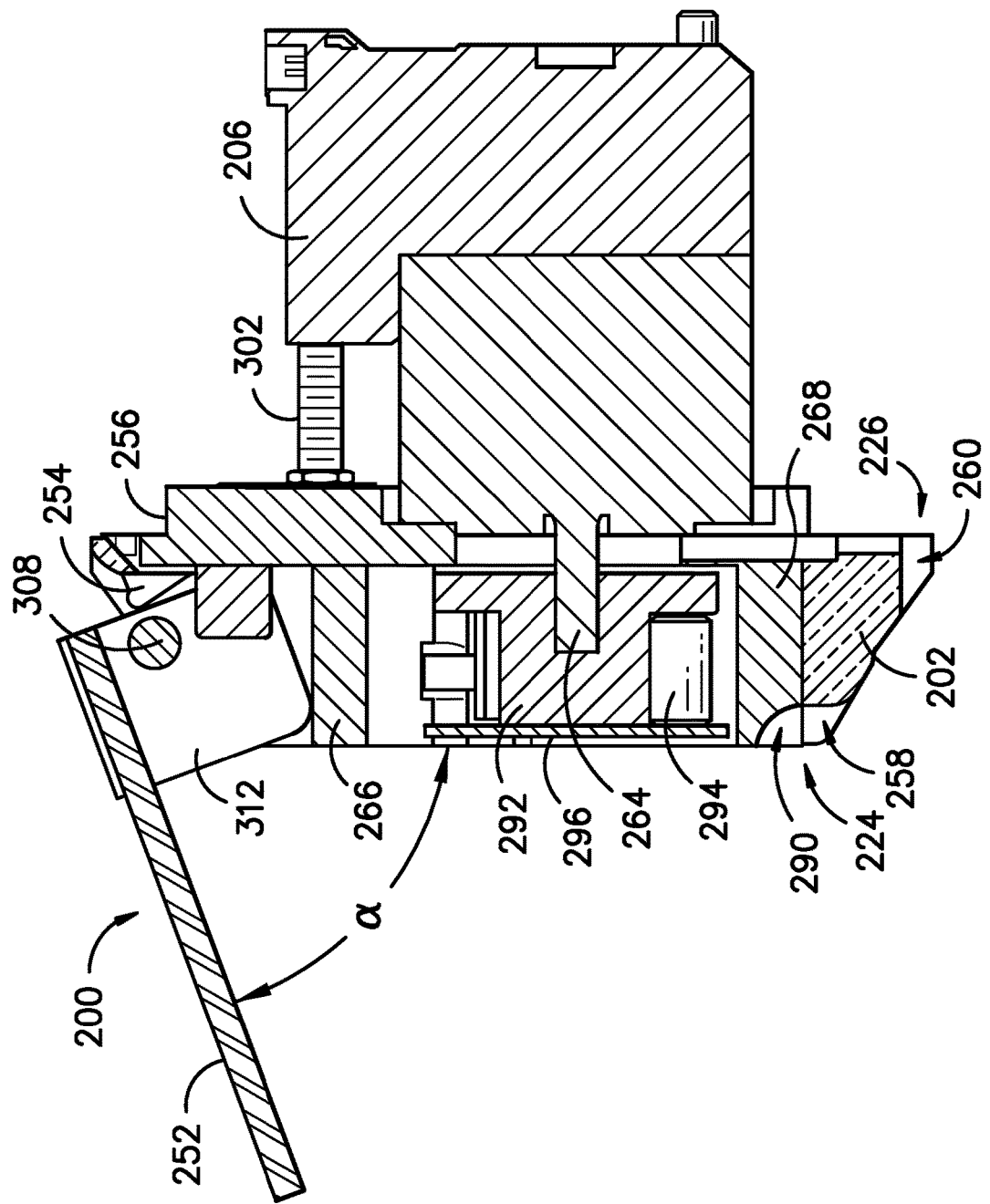
FIG. -15-

PUMP HEAD FOR A PERISTALTIC PUMP

FIELD

The present subject matter relates generally to peristaltic pumps and, more particularly, to a pump head for a peristaltic pump.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the electrode-tissue interface, allowing a higher power to be applied without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Thus, the art is continuously seeking new and improved systems and methods for treating chronic pain using cooled RF ablation techniques. For example, improved pumps for delivering cooling fluid to the active electrode during a cooled RF ablation procedure would be welcomed in the art. In particular, pump heads for peristaltic pumps that ease a tube loading process for a user would be beneficial. Further, pump heads for peristaltic pumps that reduce manufacturing costs and avoid component obsolescence issues would be useful. Accordingly, a cost effective, easy to use, and robust peristaltic pump head for a cooled RF system would be desirable.

SUMMARY

Objects and advantages of the invention will be set forth in part in the following description, or may be obvious from the description, or may be learned through practice of the invention.

In one aspect, the present subject matter is directed to a pump head for a peristaltic pump. The pump head comprises an occlusion bed, a rotor guide, a rotor assembly positioned between the occlusion bed and the rotor guide, and a pathway for tubing. The pathway comprises an inlet portion, an outlet portion, and a connecting portion that connects the inlet portion to the outlet portion. The occlusion bed is movable with respect to the rotor guide and the rotor assembly. Further, the inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly. It should also be understood that the pump head may further include any of the additional features as described herein.

In another aspect, the present disclosure is directed to a pump head for a peristaltic pump. The pump head comprises a mounting plate, an occlusion bed, a rotor guide, a rotor assembly positioned between the occlusion bed and the rotor guide, a pathway for tubing, and a cover having a closed position and an open position. The pathway comprises an inlet portion, an outlet portion, and a connecting portion that connects the inlet portion to the outlet portion. The occlusion bed, rotor guide, rotor assembly, and pathway are disposed between the mounting plate and the cover. The cover pivots between the closed position and the open position to selectively expose the occlusion bed, rotor guide, rotor assembly, and pathway. Moreover, the occlusion bed is configured to move away from the rotor guide as the cover pivots from the closed position to the open position, and the occlusion bed is configured to move toward the rotor guide as the cover pivots from the open position to the closed position. It should also be appreciated that the pump head may further include any of the additional features as described herein.

In yet another aspect, the present disclosure is directed to a pump head for a peristaltic pump. The pump head comprises an occlusion bed, a rotor guide, a rotor assembly positioned between the occlusion bed and the rotor guide, and a pathway for tubing. The pathway comprises an inlet portion, an outlet portion, and a connecting portion that connects the inlet portion to the outlet portion. The occlusion bed defines an occlusion bed recess for the rotor assembly, and the rotor guide defines a rotor guide recess for the rotor assembly. The rotor assembly is configured to rotate with respect to the occlusion bed and the rotor guide. Further, the occlusion bed is movable with respect to the rotor guide and the rotor assembly. Additionally, the inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly. The pump head urges fluid flow through the tubing to supply a cooling fluid to a medical probe assembly for delivering energy to a patient's body. The medical probe assembly comprises at least one probe having an elongate member with a distal region and a proximal region. The distal region comprises an electrically non-conductive outer circumferential portion. The medical probe assembly also comprises an electrically and thermally-conductive energy delivery device extending distally from the electrically non-conductive outer circumferential portion for delivering one of electrical and radiofrequency energy to the patient's body. The energy delivery device comprises a conductive outer circumferential surface and one or more internal lumens for circulating the cooling fluid to a distal end of the energy delivery device. It should also be understood that the pump head may further include any of the additional features as described herein.

These and other features, aspects and advantages of the present subject matter will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIG. 1 provides a schematic illustration of a portion of a pump system for applying radiofrequency electrical energy to a patient's body according to an exemplary embodiment of the present subject matter.

FIG. 2 provides a perspective view of the pump system of FIG. 1 according to an exemplary embodiment of the present subject matter.

FIG. 3 provides a block diagram of the pump system of FIG. 1 according to an exemplary embodiment of the present subject matter.

FIG. 4 provides a front, perspective view of a pump assembly according to an exemplary embodiment of the present subject matter.

FIG. 5 provides a back, perspective view of the pump assembly of FIG. 4 according to an exemplary embodiment of the present subject matter.

FIG. 6 provides a partial exploded view of the pump assembly of FIG. 4 according to an exemplary embodiment of the present subject matter.

FIG. 7 provides another partial exploded view of the pump assembly of FIG. 4 according to an exemplary embodiment of the present subject matter.

FIG. 8 provides a front view of a pump head of the pump assembly of FIG. 4 according to an exemplary embodiment of the present subject matter.

FIG. 9 provides an inlet side view of the pump head of FIG. 8 and a motor of the pump assembly of FIG. 4, according to an exemplary embodiment of the present subject matter.

FIG. 10 provides an outlet side view of the pump head of FIG. 8 and a motor of the pump assembly of FIG. 4, according to an exemplary embodiment of the present subject matter.

FIG. 11 provides a bottom side view of the pump head of FIG. 8 and a motor of the pump assembly of FIG. 4, according to an exemplary embodiment of the present subject matter.

FIG. 12 provides a perspective view of a rotor assembly of the pump assembly of FIG. 4 according to an exemplary embodiment of the present subject matter.

FIG. 13 provides a side view of the rotor assembly of FIG. 12 according to an exemplary embodiment of the present subject matter.

FIG. 14 provides a front view of the pump assembly of FIG. 4 according to an exemplary embodiment of the present subject matter.

FIG. 15 provides a cross-section view of the pump assembly of FIG. 4 according to an exemplary embodiment of the present subject matter.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of the present subject matter, a lesion refers to the region of tissue that has been irreversibly damaged as a result of the application of thermal energy, and the present subject matter is not intended to be limited in this regard. Further, for the purposes of this description, proximal generally indicates that portion of a device or system next to or nearer to a user (when the device is in use), while the term distal generally indicates a portion further away from the user (when the device is in use).

Generally, the present subject matter provides pump systems, pump assemblies, and pump heads for pumping fluid to one or more systems or assemblies. More particularly, the present subject matter provides a pump system comprising a plurality of pump assemblies, and each pump assembly of the plurality of pump assemblies supplies a fluid to a cooling circuit. The cooling circuit may be used to supply cooling fluid to the distal end of a medical probe assembly for delivering energy to a patient's body, e.g., as part of a treatment procedure. The pump system further comprises a base for supporting the plurality of pump assemblies. Each pump assembly described herein comprises a pump head, a bezel surrounding an outer perimeter of the pump head, a motor, and tubing.

In general, the pump head comprises an occlusion bed, a rotor guide, a rotor assembly positioned between the occlusion bed and the rotor guide, and a pathway for tubing. The tubing supplies fluid to the cooling circuit. The pathway comprises an inlet portion, an outlet portion, and a connecting portion that connects the inlet portion to the outlet portion. The inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly. Further, the occlusion bed is movable with respect to the rotor guide and the rotor assembly. As described herein, through such movement of the occlusion bed and other features, the pump head is configured to ease the task of inserting the tubing into the pump head such that correct insertion of the tubing is repeatable and safe. Once the tubing is inserted or loaded into the pump head, and the user is safely separated from the rotor assembly, e.g., by a rotor cover plate and pump head cover as described herein, the motor may be powered on to drive the rotor assembly and thereby begin pumping the fluid through the tubing.

Referring now to the drawings, FIG. 1 illustrates a schematic diagram of one embodiment of a system 100 of the present subject matter. As shown, the system 100 includes a generator 102; a cable 104; one or more probe assemblies 106 (only one probe assembly 106 is shown); one or more cooling devices 108; a pump cable 110; one or more proximal cooling supply tubes 112; and one or more proximal cooling return tubes 114. In an exemplary embodiment, the system 100 includes first, second, third, and fourth probe assemblies 106. As shown in the illustrated embodiment, the generator 102 is a radiofrequency (RF) generator, but optionally may be any power source that may deliver other forms of energy, including but not limited to microwave energy, thermal energy, ultrasound, and optical energy. Further, the generator 102 may include a display 103 (FIG. 2) incorporated therein. The display 103 may be operable to display various aspects of a treatment procedure, including but not limited to any parameters that are relevant to a treatment procedure, such as temperature, impedance, etc. and errors or warnings related to a treatment procedure. If no display 103 is incorporated into the generator 102, the generator 102 may include means of transmitting a signal to an external display. In one embodiment, the generator 102 is operable to communicate with one more devices, for example, with one or more of the probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 132 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two or more distal ends 132 of the cable 104 terminate in connectors 134 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102. Alternatively, the splitter 130 may include more than two distal ends. Such a connector is useful in embodiments having more than two devices connected to the generator 102, for example, if more than two probe assemblies are being used.

The cooling device(s) 108 may include any means of reducing a temperature of material located at and proximate to one or more of the probe assemblies 106. For example, as shown in FIG. 2, the cooling devices 108 may include a pump system 120 having one or more peristaltic pump assemblies 122 operable to circulate a fluid from the cooling devices 108 through one or more proximal cooling supply tubes 112, the probe assemblies 106 (via internal lumens therein, as described in greater detail below), one or more proximal cooling return tubes 114 and back to the one or more cooling devices 108. For example, as shown in the illustrated embodiment of FIGS. 2 and 3, the pump system 120 includes four peristaltic pump assemblies 122 coupled to a power supply 126. In such embodiments, as shown in FIG. 3, each of the plurality of pump assemblies 122 may be in separate fluid communication with one of the probe assemblies. The fluid may be water or any other suitable fluid or gas. In alternate embodiments, the pump system 120 may include only one peristaltic pump assembly 122 or greater than four pump assemblies 122. In addition, as shown in FIG. 3, each of the pump assemblies 122 may have an independent speed (i.e., RPM) controller 125 that is configured to independently adjust the speed of its respective pump assembly. The pump system 120 and pump assemblies 122 are described in greater detail below.

Referring to FIG. 1, the system 100 may include a controller or control module 101 for facilitating communication between the cooling devices 108 and the generator 102. In this way, feedback control is established between the cooling devices 108 and the generator 102. The feedback control may include the generator 102, the probe assemblies 106, and the cooling devices 108, although any feedback between any two devices is within the scope of the present subject matter. The feedback control may be implemented, for example, in a control module that may be a component of the generator 102. In such embodiments, the generator 102 is operable to communicate bi-directionally with the probe assemblies 106 as well as with the cooling devices 108. In the context of the present subject matter, bi-directional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements. For example, power to each of the probe assemblies 106 can be increased when a temperature measurement is low or can be decreased when a measurement is high. This variation of power may be different for each probe assembly. In some cases, the generator 102 may terminate power to one or more probe assemblies 106. Thus, the generator 102 may receive a signal (e.g., temperature measurement) from one or both of the first and second probe assemblies 106, determine the appropriate action, and send a signal (e.g., decreased or increased power) back to one or both of the probe assemblies 106. Alternatively, the generator 102 may send a signal to the cooling devices 108 to either increase or decrease the flow rate or degree of cooling being supplied to one or both of the first and second probe assemblies 106.

More specifically, the pump assemblies 122 may communicate a fluid flow rate to the generator 102 and may receive communications from the generator 102 instructing the pumps 122 to modulate this flow rate. In some instances, the peristaltic pump assemblies 122 may respond to the generator 102 by changing the flow rate or turning off for a period of time. With the cooling devices 108 turned off, any temperature sensing elements associated with the probe assemblies 106 would not be affected by the cooling fluid, allowing a more precise determination of the surrounding tissue temperature to be made. In addition, when using more than one probe assembly 106, the average temperature or a maximum temperature in the temperature sensing elements associated with the probe assemblies 106 may be used to modulate cooling.

In other embodiments, the cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density. Thus, as illustrated by these examples, the controller 101 may actively control energy delivered to the tissue by controlling an amount of energy delivered through the energy delivery device(s) 192 and by controlling a flow rate through the pump assembly(ies) 122, e.g., the flow rate through tubing of a pump head 200 of a pump assembly 122.

The cooling devices 108 may also communicate with the generator 102 to alert the generator 102 to one or more possible errors and/or anomalies associated with the cooling devices 108. Such errors and/or anomalies may include whether cooling flow is impeded or if a lid of one or more of the cooling devices 108 is opened. The generator 102 may then act on the error signal by at least one of alerting a user, aborting the procedure, and modifying an action.

The controller 101 can include various components for performing various operations and functions. For example, the controller 101 can include one or more processor(s) and one or more memory device(s). The operation of the system 100, including the generator 102 and cooling device(s) 108, may be controlled by a processing device such as the controller 101, which may include a microprocessor or other device that is in operative communication with components of the system 100. In one embodiment, the processor executes programming instructions stored in memory and may be a general or special purpose processor or microprocessor operable to execute programming instructions, control code, or micro-control code. The memory may be a separate component from the processor or may be included onboard within the processor. Alternatively, the controller 101 may be constructed without using a processor or microprocessor, e.g., using a combination of discrete analog and/or digital logic circuitry (such as switches, amplifiers, integrators, comparators, flip-flops, AND gates, and the like) to perform control functionality instead of relying upon software. Components of the system 100 may be in communication with the controller 101 via one or more signal lines or shared communication busses.

Further, the one or more memory device(s) can store instructions that when executed by the one or more processor(s) cause the one or more processor(s) to perform the operations and functions, e.g., as those described herein for communicating a signal. In one embodiment, the generator 102 includes a control circuit having one or more processors and associated memory device(s) configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements.

Such memory device(s) may generally be configured to store suitable computer-readable instructions that, when implemented by the controller(s) or processor(s) 101, configure the control circuit to perform various functions including, but not limited to, controlling an amount of energy delivered through the energy delivery device(s) 192, controlling a flow rate through the pump assembly(ies) 122, and/or other functions. More particularly, the instructions may configure the control circuit to perform functions such as receiving directly or indirectly signals from one or more sensors (e.g. voltage sensors, current sensors, and/or other sensors) indicative of various input conditions, and/or various other suitable computer-implemented functions, which enable the generator 102 or other components of system 100 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the controller(s) or processor(s) 101.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors, although other connector types are intended to be within the scope of the present subject matter.

In addition, as shown in FIG. 1, the probe assembly 106 may include a proximal region 160, a handle 180, a hollow elongate shaft 184, and a distal tip region 190 that includes the one or more energy delivery devices 192. The elongate shaft 184 and the distal tip region 190 together form a probe 186 that contact a patient's body to deliver energy thereto. The hollow elongate shaft 184 also may be described as an outer circumferential portion 184 of the probe 186, and the energy delivery device 192 extends distally from the outer circumferential portion 184. As further described herein, the elongate shaft 184 may be an electrically non-conductive outer circumferential portion 184, e.g., the shaft 184 may be formed from an electrically non-conductive material or may be electrically insulated, and the energy delivery device(s) 192 may be electrically and thermally-conductive energy delivery device(s) 192.

The proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106 but alternate embodiments with rigid tubes are possible. Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe assembly 106 also may include a shaft supply tube 136 and a shaft return tube 138, which are internal lumens for circulating cooling fluid to a distal end of the probe assembly 106. The distal cooling supply tube 162 and the distal cooling return tube 164 may be connected to the shaft supply tube 136 and the shaft return tube 138, respectively, within the handle 180 of the probe assembly 106. In one embodiment, the shaft supply tube 136 and the shaft return tube 138 may be hypotubes made of a conductive material, such as stainless steel, that extend from the handle 180 through a lumen of the hollow elongate shaft 184 to distal tip region 190. The number of hypotubes used for supplying cooling fluid and the number used for returning cooling fluid and the combination thereof may vary and all such combinations are intended to be within the scope of the present invention. As illustrated in FIG. 1, the cooling fluid flows in a cooling circuit 140 formed by the cooling device(s) 108, the distal tip region 190 of the probe, and the various supply and return tubes 112, 114, 162, 162, 136, 138. The arrows FF in FIG. 1 illustrate the direction of flow of the cooling fluid supplied by the cooling device(s) 108 through the cooling circuit 140. More specifically, the cooling fluid flows from the cooling device(s) 108, through proximal cooling supply tube 112 to distal cooling supply tube 162, through distal cooling supply tube 162 to shaft supply tube 136, through shaft supply tube 136 to the distal tip region 190, from the distal tip region 190 to shaft return tube 138, through shaft return tube 138 to distal return tube 164, through distal return tube 164 to proximal return tube 114, and through proximal return tube 114 to the cooling device(s) 108.

Referring still to FIG. 1, the probe cable connector 172 may be located at a proximal end of the probe assembly cable 170 and may be operable to reversibly couple to one of the connectors 134, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192, as well as to connect multiple temperature sensing elements to the generator 102.

In addition, the handle 180 may be operable to easily and securely couple to an optional introducer tube, e.g., in an embodiment where an introducer tube would facilitate insertion of the one or more probe assemblies 106 into a patient's body. For instance, as shown, the handle 180 may taper at its distal end to accomplish this function, i.e., to enable the handle 180 to securely couple to an optional introducer tube. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with the handle 180 of a probe assembly 106. An introducer tube may be used to gain access to a treatment site within a patient's body, and the hollow elongate shaft 184 of a probe assembly 106 may be introduced to the treatment site through the longitudinal bore of the introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The introducer tubes may be made of various materials, as is known in the art and, if the material is electrically conductive, the introducer tubes may be electrically insulated along all or part of their length, to prevent energy from being conducted to undesirable locations within a patient's body. In some embodiments, the elongate shaft 184 may be electrically conductive, and an introducer may function to insulate the shaft 184, leaving the energy delivery device 192 exposed for treatment. Further, the introducer tubes may be operable to connect to a power source and, therefore, may form part of an electrical current impedance monitor (wherein at least a portion of the introducer tube is not electrically insulated). Different tissues may have different electrical impedance characteristics, and therefore, it is possible to determine tissue type based on impedance measurements, as has been described. Thus, it would be beneficial to have a means of measuring impedance to determine the type of tissue within which a device is located. In addition, the gauge of the introducer tubes may vary depending on the procedure being performed and/or the tissue being treated. In some embodiments, the introducer tubes should be sufficiently sized in the radial dimension so as to accept at least one probe assembly 106. Moreover, in alternative embodiments, the elongate shaft 184 may be insulated so as not to conduct energy to portions of a patient's body that are not being treated.

The system 100 also may include one or more stylets. A stylet may have a beveled tip to facilitate insertion of the one or more introducer tubes into a patient's body. Various forms of stylets are well known in the art and the present subject matter is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the generator 102 may receive impedance measurements from one or more of the stylets, the introducer tubes, and/or the probe assemblies 106 and may perform an action, such as alerting a user to an incorrect placement of an energy delivery device 192, based on the impedance measurements.

The energy delivery devices 192 may include any means of delivering energy to a region of tissue adjacent to the distal tip region 190. For example, the energy delivery devices 192 may include an ultrasonic device, an electrode, or any other energy delivery means, and the present subject matter is not limited in this regard. Similarly, energy delivered via the energy delivery devices 192 may take several forms, including but not limited to thermal energy, ultrasonic energy, radiofrequency energy, microwave energy, or any other form of energy. For example, in one embodiment, the energy delivery devices 192 may include an electrode. The active region of the electrode 192 may be 2 to 20 millimeters (mm) in length and energy delivered by the electrode is electrical energy in the form of current in the RF range. The size of the active region of the electrode can be optimized for placement within, e.g., an intervertebral disc; however, different sizes of active regions, all of which are within the scope of the present subject matter, may be used depending on the specific procedure being performed. In some embodiments, feedback from the generator 102 may automatically adjust the exposed area of the energy delivery device 192 in response to a given measurement, such as impedance or temperature. For example, in one embodiment, the energy delivery devices 192 may maximize energy delivered to the tissue by implementing at least one additional feedback control, such as a rising impedance value. As previously described, each energy delivery device 192 may be electrically and thermally-conductive and may comprise a conductive outer circumferential surface to conduct electrical energy and heat from the distal tip region 190 of the probe 186 to a patient's body. Further, the distal tip region 190 includes one or more temperature sensing elements, which are operable to measure the temperature at and proximate to the one or more energy delivery devices 192. The temperature sensing elements may include one or more thermocouples, thermometers, thermistors, optical fluorescent sensors or any other means of sensing temperature.

In one embodiment, the first and second probe assemblies 106 may be operated in a bipolar mode. For example, the distal tip region 190 of each of two probe assemblies may be located within an intervertebral disc. In such embodiments, electrical energy is delivered to the first and second probe assemblies 106, and this energy is preferentially concentrated therebetween through a region of tissue to be treated (i.e., an area of the intervertebral disc). The region of tissue to be treated is thus heated by the energy concentrated between the first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies 100. For example, in some embodiments, three probe assemblies 106 may be used, and the probe assemblies 106 may be operated in a triphasic mode, whereby the phase of the current being supplied differs for each probe assembly 106. In further embodiments, the system 100 may be configured to control one or more of the flow of current between electrically conductive components and the current density around a particular component. In such embodiments, the system 100 may be configured to alternate between monopolar configurations, bipolar configurations, or quasi-bipolar configurations during a treatment procedure.

As a particular example, to treat tissue of a patient's body according to an exemplary embodiment of the present subject matter, the energy delivery device 192 of each of two probe assemblies 106 may be inserted into the patient's body, e.g., using an introducer and stylet as described herein. Once a power source, such as the generator 102, is connected to the probe assemblies 106, a stimulating electrical signal may be emitted from either of the electrodes 192 to a dispersive electrode or to the other electrode 192. This signal may be used to stimulate sensory nerves, where replication of symptomatic pain would verify that the tissue, such as an intervertebral disc, is pain-causing. Simultaneously, the cooling fluid may be circulated through the internal lumens 136, 138 of the probe assemblies 106 via the pump assemblies 122 and energy may be delivered from the RF generator 102 to the tissue through the energy delivery devices 192. In other words, radiofrequency energy is delivered to the electrodes 192 and the power is altered according to the temperature measured by the temperature sensing element in the tip of the electrodes 192 such that a desired temperature is reached between the distal tip regions 190 of the two probe assemblies 106. During the procedure, a treatment protocol such as the cooling supplied to the probe assemblies 106 and/or the power transmitted to the probe assemblies 106 may be adjusted and/or controlled to maintain a desirable treatment area shape, size and uniformity. More specifically, actively controlling energy delivered to the tissue by controlling both an amount of energy delivered through the energy delivery devices 192 and individually controlling the flow rate of the pump assemblies 122. In further embodiments, the generator 102 may control the energy delivered to the tissue based on the temperature measured by the temperature sensing element(s) in the distal tip region 190 of the probe assemblies 106 and/or based on impedance sensors.

Referring now to FIG. 2 and FIGS. 4-15, the pump system 120 and pump assemblies 122 will be described in greater detail. As previously described, FIG. 2 illustrates a pump system 120 having a plurality of pump assemblies 122. In the depicted embodiment, the pump system 120 comprises four pump assemblies 122. Each pump assembly 122 supplies a fluid to a probe assembly 106 via the cooling circuit 140, which includes a cooling device 108 and its associated cooling supply tube and connector 112, 116 and cooling return tube and connection 114, 118, as well as the cooling supply tube and connector 162, 166, cooling return tube and connector 164, 168, and internal lumens (i.e., shaft supply and return tubes) 136, 138 of the probe assembly 106. As further illustrated in FIG. 2, a base 142 supports the plurality of pump assemblies 122. More particularly, the base 142 defines a plurality of openings 144, and each opening 144 receives one of the plurality of pump assemblies 122. In the depicted embodiment, the base 142 defines four openings 144, one for each of the four pump assemblies 122, but the base may define any number of openings 144. The base 142 further defines various channels 146, which may direct fluid away from the pump system 120, e.g., in the event cooling fluid overflows or escapes from the cooling circuit 140.

As shown most clearly in FIGS. 4-7, each pump assembly 122 of the plurality of pump assemblies 122 comprises a pump head 200, a bezel 202 surrounding the pump head 200, a motor 206, and tubing 208 (FIG. 2). More specifically, the pump head 200 is received in an opening 201 defined by the bezel 202 such that the bezel 202 surrounds an outer perimeter 204 of the pump head 200, and a separate tubing 208 may be provided for each pump assembly 122. In exemplary embodiments, the tubing 208 may be formed from an elastomeric material having a durometer within a range of about 50 to about 70 Shore A hardness, and the tubing may have an outer diameter or approximately 3/16" (three sixteenths of an inch) and an inner diameter of approximately 1/16" (one sixteenth of an inch). Of course, other appropriate types of materials with suitable durometers also may be used, and tubing 208 have different dimensions, such as an outer diameter within a range of about 1/8" (one eighth of an inch) to about 1/2" (one half of an inch) and an inner diameter within a range of about 1/32" (one thirty-second of an inch) to about 3/8" (three eighths of an inch), may be used as well. Further, various fasteners may be used to fasten components of the pump assembly 122 to one another. For example, referring to FIG. 6, fasteners 207 such as self-tapping screws or the like may be used to fasten brackets 244, 246 to the bezel 202, and fasteners 209 may be used to fasten the motor 206 to the bezel 202. The fasteners may be suitable mechanical fasteners, or other types of fasteners or methods for securing components to one another, such as welding, ultrasonic welding, interference fits, etc., may be used to hold the components of the pump assembly 122 in position in the pump system 120 or with respect to one another.

A fluid source 210 (FIG. 2) supplies the cooling fluid to the cooling circuit 140. For example, the tubing 208 is fluidly connected to the fluid source 210, such that the cooling fluid flows from the fluid source 210 into the tubing 208 and, from the tubing 208, into the remainder of the cooling circuit 140 to cool the distal end 194 of the energy delivery device 192 of the probe assembly 106, as described in greater detail herein. As previously stated, in exemplary embodiments, each pump assembly 122 is a peristaltic pump, and the pump head 200 is configured to supply the cooling fluid to the cooling circuit 140 by compressing the tubing 208 at various points within the pump assembly 122, urging fluid from the fluid source 210 to flow from an inlet side 212 of the pump assembly 122 to an outlet side 214 of the pump assembly 122 and thereon to the lumens 136, 138 and the distal end 194 of the energy delivery device 192. The pump head 200 is described in greater detail herein.

As shown, for instance, in FIG. 6, the bezel 202 comprises a bezel upper side 216, a bezel lower side 218 that is opposite the bezel upper side 216, a bezel inlet side 220 extending from the bezel upper side 216 to the bezel lower side 218, and a bezel outlet side 222 that is opposite the bezel inlet side 220 and that extends from the bezel upper side 216 to the bezel lower side 218. Further, the bezel 202 comprises a bezel top side 224 and a bezel bottom side 226. The bezel top side 224 defines a bezel top perimeter 228, which extends around each of the bezel upper, lower, inlet, and outlet sides 216, 218, 220, 222, and the bezel bottom side 226 defines a bezel bottom perimeter 230 which extends around each of the bezel upper, lower, inlet, and outlet sides 216, 218, 220, 222 opposite the bezel top perimeter 228. The bezel top perimeter 228 is smaller than the bezel bottom perimeter 230 such that, as illustrated in the figures, the bezel 202 flares outward from the bezel top side 224 to the bezel bottom side 226.

Referring to FIGS. 4, 6, and 14, the bezel 202 defines an inlet channel 232 on the bezel inlet side 220 and an outlet channel 234 on the bezel outlet side 222. Each of the inlet channel 232 and the outlet channel 234 guide the tubing 208 into the pump head 200. Moreover, the inlet channel 232 has a first inlet width $w_{inlet1}$ adjacent an inner surface 236 of the bezel inlet side 220 and a second inlet width $w_{inlet2}$ adjacent an outer surface 238 of the bezel inlet side 220. The second inlet width $w_{inlet2}$ is wider than the first inlet width $w_{inlet1}$ such that the inlet channel 232 flares away from the pump head 200. Similarly, the outlet channel 234 has a first outlet width $w_{outlet1}$ adjacent an inner surface 240 of the bezel outlet side 222 and a second outlet width $w_{outlet2}$ adjacent an outer surface 242 of the bezel outlet side 222. Like the first and second inlet widths $w_{inlet1}$, $w_{inlet2}$, the second outlet width $w_{outlet2}$ is wider than the first outlet width $w_{outlet1}$ such that the outlet channel 234 flares away from the pump head 200. The flared inlet and outlet channels 232, 234 of the bezel 202 may help a user guide the tubing 208 into the pump head 200, e.g., such that the tubing 208 is correctly seated in the pump head 200 every time a user loads tubing 208 into the pump head 200. Further, the flared channels 232, 234 also provide the tubing 208 some space to move with respect to the bezel 202, e.g., to help in guiding the tubing 208 into the pump head 200, to help prevent tubing migration as described in greater detail herein, etc.

As shown most clearly in FIG. 6, an inlet bracket 244 is attached to the inner surface 236 of the bezel inlet side 220, and an outlet bracket 246 is attached to the inner surface 240 of the bezel outlet side 222. The inlet bracket 244 defines an inlet bracket groove 248 for receipt of the tubing 208 on the bezel inlet side 220, and the outlet bracket 246 defines an outlet bracket groove 250 for receipt of the tubing 208 on the bezel outlet side 222. As described in greater detail herein, the inlet bracket groove 248 and the outlet bracket groove 250 work with grooves defined in the pump head 200, e.g., to hold the tubing 208 in place with respect to the pump assembly 122.

The figures also depict that the pump head 200 comprises a pivotable pump head cover 252, which may be transparent or translucent to allow a user to see through the cover 252 when it is in a closed position, e.g., to view the tubing 208 installed or loaded within the pump head 200. Referring to FIGS. 4, 6, and 7, the bezel 202 defines at least one stop 254 for limiting an angular range of motion of the pump head cover 252, as illustrated in FIG. 15. That is, the cover 252, or one or more components attached to the cover 252 (e.g., to enable the cover 252 to pivot with respect to the pump head 200) contacts the stop(s) 254 when the cover 252 attains a particular angular position with respect to the pump head 200, e.g., when the cover 252 is at a maximum angle α with respect to the pump head 200. For instance, as shown in FIG. 15, the stop(s) 254 may prevent the pump head cover 252 from opening or pivoting more than about 70° away from the pump head 200. That is, the stops 254 have a shape or size, or a position in the bezel 202, to contact the cover 252 (or an attached component) when the cover 252 reaches a given angular position with respect to the pump head 200, thereby preventing the pump head cover 252 from rising away from the pump head 200 above the given angle. In other embodiments, the angular range of motion of the pump head cover 252 may be limited to other angular positions; for example, the angular position of the cover 252 may be limited to an angle within a range of about 60° to about 90° with respect to the pump head 200, although other angular values may be used as well. Limiting the angular range of motion of the pump head cover 252 limits, for example, the width W of a pathway 274 for the tubing 208 defined within the pump head 200. As further described herein, the tubing pathway 274 opens as the cover 252 is lifted away from the pump head 200, and the width of such pathway is determined by the extent to which the cover 252 opens (or the angle α between the cover 252 and pump head 200).

Limiting the width W of the tubing pathway 274 may have benefits such as providing a relatively precise opening for the tubing 208, thereby easing the task of loading the tubing 208 in the pump head 200, and enhancing the safety of the assembly 122, e.g., by preventing a user from catching an appendage or other object in the pump head 200.

As further depicted in the figures, the pump head comprises a mounting plate 256 opposite the pump head cover 252. More particularly, the pump head cover 252 is disposed adjacent the bezel top side 224, and the pump head mounting plate 256 is disposed adjacent the bezel bottom side 226. As shown in FIG. 5, the mounting plate 256 may be recessed in the bottom of the bezel 202, i.e., the mounting plate 256 may fit within a recess defined in the bezel bottom side 226.

Further, the bezel 202 defines a depression 258 in the bezel top side 224 to provide finger space for a user of the pump assembly 122 to open the pump head cover 252. Moreover, the bezel 202 defines an opening 260 in the bezel bottom side 226 to allow fluid to flow away from the pump assembly 122. Similarly, as illustrated in FIGS. 8 and 11, the mounting plate 256 comprises an upper portion 256a and an opposite lower portion 256b, and the lower portion 256b defines an opening 257 therein for fluid to flow away from the pump head 200. The opening 257 may be a channel extending from the space in which a rotor assembly of the pump head 200 is positioned to the lower portion 256b of the mounting plate 256. The opening 257 at the mounting plate lower portion 256b may align with the opening 260 in the bezel bottom side 226. The openings 257, 260 may allow fluid to flow out of the rotor space, e.g., in the event the tubing 208 is compromised and the cooling fluid ingresses into the rotor assembly, and away from the pump head 200 and pump assembly 122. Additionally, it will be appreciated that the bezel 202 may be molded from a thermoplastic material or the like; for example, the bezel 202 may be injection molded from a thermoplastic material. As such, the stop(s) 254, depression 258, and/or opening 260, as well as other features of the bezel 202, may be molded-in features of the bezel 202. Of course, in other embodiments, such features also may be formed in other ways.

Additionally, as shown in FIGS. 4-7, 9-11, and 15, the pump assembly motor 206 is in operative communication with a rotor assembly 262 of the pump head 200 to drive the rotor assembly 262, producing a peristaltic effect on the tubing 208 and thereby moving the cooling fluid through the tubing 208. More particularly, a rotor or shaft 264 of the motor 206 is coupled to the rotor assembly 262 to position the motor 206 in operative communication with the pump head rotor assembly 262. Further, as illustrated in FIG. 2, the openings 144 in the base 142 allow the motor 206 of each pump assembly 122 to extend into the base 142. Thus, the motors 206 of the plurality of pump assemblies 122 are, e.g., out of the way of the tubing 208 and fluid source(s) 210. Moreover, in exemplary embodiments, each motor 206 may be a stepper motor, but other suitable types of motors for driving the rotor assembly 264 may be used as well. No matter its type, each motor 206 may include an integrated motion controller that receives inputs, such as analog signals, and outputs rotational speed through the rotor 264. The rotor 264 rotates in a clockwise or counterclockwise direction at the rotational speed dictated by the motor's integrated motion controller; the rotational speed and direction are transmitted to the rotor assembly 262 via the rotor 264, which is coupled to the rotor assembly 262. The rotational direction of the rotor 264 may be programmed into the controller of the motor 206. The pump head rotor assembly 262 will be described in greater detail herein.

Referring now to FIGS. 8 and 14, the pump head 200 further comprises an occlusion bed 266 and a rotor guide 268, which, with the rotor assembly 262, help guide the tubing 208 through the pump head 200. More particularly, the rotor guide 268 defines a rotor guide recess 270 into which the rotor assembly 262 is received. The occlusion bed 266 further defines an outline that fits around the rotor assembly 262. Accordingly, the rotor assembly 262 is positioned between the occlusion bed 266 and the rotor guide 268. Referring particularly to FIG. 14, the occlusion bed 266 is movable with respect to the rotor guide 268 and the rotor assembly 262. As illustrated, the pump head 200 includes a pair of guide rails 272, although in other embodiments, the pump head 200 may include only one or more than two guide rails 272. The occlusion bed 266 is received on the guide rails 272 such that the guide rails 272 guide the occlusion bed 266 as the occlusion bed 266 moves with respect to the rotor guide 268 and rotor assembly 262. As explained in greater detail herein, when the pivotable pump head cover 252 is pivoted toward or away from the pump head 200, the occlusion bed 266 moves, within the opening 201 for the pump head 200 defined by the bezel 202, with respect to the rotor guide 268 and the rotor assembly 262.

Movement of the occlusion bed 266 away from the rotor guide 268 and rotor assembly 262 exposes a pathway 274 for the tubing 208. The pathway 274 comprises an inlet portion 274a, an outlet portion 274b, and a connecting portion 274c that connects the inlet portion 274a to the outlet portion 274b. As depicted in FIG. 14, the inlet portion 274a of the pathway 274 is defined between the occlusion bed 266 and the rotor guide 268, and similarly, the outlet portion 274b is defined between the occlusion bed 266 and the rotor guide 268. The connecting portion 274c, connecting the inlet and outlet portions 274a, 274b, is defined between the occlusion bed 266 and the rotor assembly 262. As shown in the figures, the inlet portion 274a slopes or is angled toward the pump midline ML, and the outlet portion 274b slopes or is angled away from the midline ML. Further, the connection portion 274c is generally arced or curved, following along the outside of a generally cylindrical shape defined by the rotor assembly 262.

As shown in FIGS. 8 and 14, the pump head cover 252 has a closed position and an open position. The cover 252 pivots with respect to the mounting plate 256 to alternate between the closed position and the open position and, thereby, to selectively expose the occlusion bed 266, rotor guide 268, rotor assembly 262, and pathway 274 to access by a user. If tubing 208 is loaded into the pump head 200, when the pump head cover 252 is in its closed position, illustrated in FIG. 8, the tubing 208 is clamped between the occlusion bed 266 and the rotor guide 268, as well as between the occlusion bed 266 and rotor assembly 262 at the connecting portion 274c of the pathway 274. When the pump head cover 252 is in its open position, as illustrated in FIG. 14, the occlusion bed 266 is separated from the rotor guide 268 and the rotor assembly 262 by the pathway 274, which allows the tubing 208 to be loaded into the pump head 200 and onto the rotor assembly 262 or allows the tubing 208 to be removed from the pump head 200. Thus, the cover 252 pivots between the closed position and the open position to selectively expose the occlusion bed 266, rotor guide 268, rotor assembly 262, and pathway 274. Further, the occlusion bed 266 is configured to move away from the rotor guide 268 and rotor assembly 262 as the cover 252 pivots from the closed position to the open position, and the occlusion bed 266 is configured to move toward the rotor guide 268 and rotor assembly 262 as the cover 252 pivots from the open position to the closed position.

As previously described, the stop(s) 254 on the bezel 202 limit the opening of the cover 252, which in turn limits the movement of the occlusion bed 266 with respect to the rotor guide 268 and rotor assembly 262. That is, the distance the occlusion bed 266 moves away from the rotor guide 268 and rotor assembly 262, e.g., by sliding along the guide rail(s) 272 as described herein, is limited by the degree to which the pump head cover 252 can be opened. Thus, the maximum angular position of the cover 252 with respect to the pump head 200 may be selected based on a desired distance between the occlusion bed 266 and the rotor guide 268 and rotor assembly 262, i.e., the width W of the pathway 274. The distance between the upper occlusion bed 266 and the lower rotor guide 268 and rotor assembly 262, when the occlusion bed 266 is separated from the lower components, may be selected to provide a width W of the pathway 274 that eases the process for a user of loading the tubing 208 into the pump head 200 by creating a guided pathway 274 for the tubing 208 without providing too large of an area—in which the tubing could become kinked, etc. or a user could stick a finger or other portion of the user's hand, which then could be pinched when the cover 252 is lowered—and without providing too small of an area, in which the tubing 208 cannot fit into the pump head 200. Further, the occlusion bed 266, rotor guide 268, rotor assembly 262, and pathway 274 are disposed between the cover 252 and the mounting plate 256 such that the pathway 274 is inaccessible by a user of the pump head 200 when the cover 252 is in the closed position but is accessible by the user when the cover 252 is in the open position. Thus, the limited range of motion of the cover 252 and occlusion bed 266, as well as the position of the pathway 274 within the pump assembly 122, helps prevent the user from misloading the tubing into the pump head 200, as well as enhances the safety of the pump assembly 122.

Referring now to FIGS. 9 and 10, the rotor guide 268 has a rotor guide inlet side 276 that defines a rotor guide inlet groove 278 and a rotor guide outlet side 280 that defines a rotor guide outlet groove 282. In the depicted embodiment, each of the rotor guide inlet and outlet grooves 278, 282 are generally V-shaped notches extending into the rotor guide 268 from the respective rotor guide inlet and outlet sides 276, 280. On the inlet side 212 of the pump assembly 122, the tubing 208 is seated on the rotor guide inlet groove 278, and on the outlet side 214 of the pump assembly 122, the tubing 208 is seated on the rotor guide outlet groove 282. As further shown, e.g., in FIGS. 4 and 7, when the pump head 200 is assembled with the bezel 202, the inlet bracket groove 248 aligns with the rotor guide inlet groove 278 and the outlet bracket groove 250 aligns with the rotor guide outlet groove 282. The inlet bracket groove 248 and rotor guide inlet groove 278 guide the tubing 208 into the inlet portion 274a of the pathway 274, and the outlet bracket groove 250 and rotor guide outlet groove 282 guide the tubing 208 out of the outlet portion 274b of the pathway 274. Further, the inlet and outlet brackets 244, 246 and the rotor guide grooves 278, 282 help hold the tubing 208 in place with respect to the pump assembly 122.

As further illustrated in FIGS. 9 and 10, the occlusion bed 266 has an occlusion bed inlet side 284 and an occlusion bed outlet side 286. The occlusion bed 266 also defines a slot 288 for the tubing 208. More particularly, the slot 288 is defined from the occlusion bed outlet side 286 toward a midline ML (FIG. 8) of the pump head 200. In exemplary embodiments, the slot 288 tapers from the occlusion bed outlet side 286 toward the midline ML. As previously stated, the tubing 208 is seated on the rotor guide inlet groove 278 on the inlet side 212 of the pump assembly 122, and on the outlet side 214 of the pump assembly 122, the tubing 208 is seated on the rotor guide outlet groove 282. The occlusion bed 266 compresses the tubing 208 on the inlet side 212 to prevent slippage during pumping, i.e., when the rotor assembly 262 is rotating to intermittently compress the tubing 208 and thereby move fluid therethrough. However, the compression of the tubing 208 between the occlusion bed inlet side 284 and the rotor guide inlet groove 278 is not enough to occlude the flow of fluid through the tubing 208. That is, the occlusion bed 266 compresses the tubing 208 enough to prevent slippage but not enough to occlude flow through the tubing 208. Further, the slot 288 prevents the occlusion bed 266 from compressing the tubing 208 on the outlet side 214. That is, the tubing 208 is seated on the rotor guide outlet groove 282 but is not compressed by the occlusion bed 266 because of the opening, i.e., slot 288, in the occlusion bed 266 on its outlet side 286, which provides more space for the tubing 208 on the outlet side 214 than on the inlet side 212 (where the tubing is slightly compressed by the occlusion bed as described), and the tubing 208 is free to move into the space provided by the slot 288. Thus, any growth in the length of the tubing 208 within the rotor space during pumping, e.g., due to stretching of the tubing 208 as the rotor assembly 262 rotates against the tubing 208, is fed out of the rotor space and into the opening defined by the slot 288 and rotor guide outlet groove 282 on the outlet side 214, thereby allowing minimal tubing migration on the rotor assembly 262.

Moreover, as depicted in FIGS. 9 and 10, the pump head cover 252 extends over and adjacent the occlusion bed 266 and rotor guide 268 when the cover 252 is in its closed position. Referring to FIGS. 8, 11, and 14, the rotor guide 268 defines a depression 290 to provide finger space for a user to open the cover 252. That is, the depression 290 allows the user to, e.g., stick one or more fingers under the cover 252 and lift the cover 252 away from the rotor guide 268 and occlusion bed 266. Of course, rather than using his or her fingers, the user also may use a tool, instrument, or other object to lift the cover 252. Further, as illustrated in FIG. 14, the depression 290 in the rotor guide 268 aligns with the depression 258 in the bezel 202 when the pump head 200 is assembled with the bezel 202 to give the user sufficient space in the assembly 122 to insert an object and lift the pump head cover 252.

Referring now to FIGS. 12 and 13, the rotor assembly 262 will be described in greater detail. As shown in the figures, the rotor assembly 262 comprises a mounting block 292, a plurality of roller bearings 294, and a cover plate 296. The rotor or shaft 264 of the assembly motor 206 is positioned in operative communication with the mounting block 292 to drive the rotor assembly 262. More particularly, the rotor 264 is received by the mounting block 292 to place the motor 206 in operative communication with the rotor assembly 262. For example, the mounting block 292 may be secured to the rotor 264 by a set screw or the like extending through an aperture or tapped hole 298 in the mounting block 292 into the rotor 264. Further, as previously stated, in exemplary embodiments, the pump assembly 122 is a peristaltic pump assembly, such that the rotor assembly 262 generates a peristaltic effect to move the cooling fluid through the tubing 208. The rotor assembly 262 is configured to rotate with respect to the occlusion bed 266 and the rotor guide 268 to urge fluid flow through the tubing 208 to supply the cooling fluid to a medical probe assembly 106. As previously described, the motor 206 dictates the direction of rotation of the rotor assembly 262, clockwise or counter-clockwise. A directional mark 295, such as the arrow 295 shown on the occlusion bed 266 in FIGS. 8 and 14, may be printed on, etched in, molded in, or otherwise defined on the pump head 200 to indicate the rotor assembly's direction of rotation to a user. In the depicted embodiment, the rotor assembly 262 rotates counter-clockwise.

The roller bearings 294 are evenly spaced along the circumference of the mounting block 292; in the depicted embodiment, the rotor assembly 262 includes four roller bearings 294 spaced equidistantly from one another about the mounting block circumference. The roller bearings 294 and mounting block 292 form a generally cylindrical shape. The cover plate 296 covers the rotor assembly 262 adjacent the pump head cover 252. In the illustrated exemplary embodiment, the cover plate 296 is secured to each roller bearing 294; a mechanical fastener 300, such as a screw or the like, extends through the cover plate 296 into the center of a roller bearing 294 to fasten the cover plate 296 to the rotor assembly 262. The cover plate 296 helps define the connecting portion 274c of the pathway 274 to help prevent a user from misloading the tubing 208 onto the roller bearings 294. Moreover, the connecting portion 274c of the pathway 274 is defined between the rotor assembly 262 and the occlusion bed 266 such that the tubing 208 contacts at least one roller bearing 294 of the plurality of roller bearings 294 within the pathway connecting portion 274c. That is, as shown in FIG. 13, a space is defined between the cover plate 296 and a back plate 293 of the mounting block 292, providing space for the tubing 208 to rest on the roller bearings 294. It will be appreciated that, as the rotor assembly 262 rotates, the roller bearing(s) 294 in contact with the tubing 208 change, e.g., the tubing 208 may contact a first roller bearing 294 and a second roller bearing 294 at a first point in time, the second roller bearing 294 and a third roller bearing 294 and a second point in time, the third roller bearing 294 and a fourth roller bearing at a third point in time, etc. Further, the cover plate 296 provides a sufficient gap G between the rotor assembly 262 and the occlusion bed 266 for the tubing 208 to be inserted into the pathway 274, but in exemplary embodiments, the gap G is insufficient for the user to stick one of the user's fingers or the like into the pathway 274. Thus, the cover plate 296 helps ease the tube loading process while also increasing the safety of, or reducing the risk of injury to the user from, the tube loading process.

As illustrated in FIGS. 5-7, 9-11, and 15, the pump head 200 includes a closure detection mechanism 302 that senses whether the pump head cover 252 is open or closed. The closure detection mechanism 302 comprises a first element 304 on the cover 252 and a second element 306 on the pump head mounting plate 256 or other suitable stationary component of the pump head 200. In the illustrated exemplary embodiment, the closure detection mechanism 302 is a magnetic reed switch, comprising a magnet as the first element 304 and a sensor as the second element 306. The magnet first element 304 on the cover 252 activates the sensor second element 306. When the cover 252 is in its closed position, the magnet first element 304 is near the sensor second element 306 such that a switch is closed, completing a circuit and allowing power to the motor 206 for its operation (i.e., rendering the motor 206 operable), which in turn causes the rotor assembly 262 to rotate. When the cover 252 is opened, the magnet first element 304 moves away from the sensor second element 306, and when the magnet 304 is a certain distance from the sensor 306, the switch and circuit are electrically open and the power to the motor 206 is interrupted or cut, thereby stopping the rotation of the rotor assembly 262. It will be appreciated that the cover 252 need not be opened as far as it possibly can be opened before the switch is opened and power to the motor 206 is terminated; however, the circuit is open when the cover 252 is in its open position. Thus, the closure detection mechanism 302 acts, at least in part, as a safety feature of the pump assembly 122, stopping rotation of the rotor assembly 262 by rendering the motor 206 inoperable when a user may be reaching into the pump head 200, which is accessible through the open cover 252. Further, other types of mechanisms, such as a mechanical or optical switch, may be used in place of the magnetic reed switch.

Moreover, referring for example to FIG. 8, the gaps or spaces between the occlusion bed 266 and rotor guide 268, as well as between other components of the pump head 200 affected by the pivoting motion of the pump head cover 252, may be minimized to maximize the tolerance for opening the cover 252 without interrupting the power to the motor 206. More specifically, by minimizing the gaps between components such as the occlusion bed 266 and rotor guide 268 when the cover 252 is in its closed position, the cover 252 has more "play" in its movement before the motor 206 cuts off. That is, the cover 252 can move more, or has a greater angular range of motion, before the closure detection mechanism 302 disengages the motor 206 from its power source. As an example, one safety standard would require the motor 206 to be stopped if the gap G exceeded four millimeters (4 mm). Thus, by minimizing the gap G when the cover 252 is in its closed position (i.e., ensuring the gap G is as close to 0 mm as possible), the cover 252, as well as the occlusion bed 266, may travel a greater distance before the motor 206 is inoperable compared to a design in which the gap G is near 4 mm when the cover is in its closed position. Such a minimal gap design may help improve the accuracy of the closure detection mechanism 302, e.g., by working within the tolerance of the closure detection mechanism 302 between closed and open states.

Further, minimizing the gaps also may help limit the width W of the pathway 274 to just wide enough for the tubing 208. As previously explained, because the cover 252 controls the movement of the occlusion bed 266, the extent to which the cover 252 may open (i.e., the maximum angle between the cover and the remainder of the pump head 200) may be limited to limit the width W of the pathway 274 such that a user's finger or the like cannot be caught in the pump head 200. By minimizing the gaps, such as gap G, between the components when the cover 252 is closed, the cover 252 may travel a greater angular distance (i.e., have a greater maximum angle from the pump head 200) before the pathway 274 achieves its optimum width W for safe and easy loading of the tubing 208. Thus, the greater maximum opening angle of the pump head cover 252 may provide a more comfortable or easy loading configuration for the user while improving the precision of the tubing pathway width W.

The pump head 200 further comprises a tension bar 308 and occlusion cams 310, 312, which are shown most clearly in FIG. 6. The bar 308 and cams 310, 312, e.g., control the movement of the occlusion bed 266 with respect to the rotor guide 268 and rotor assembly 262. More particularly, the tension bar 308 has a tension bar inlet end 314, to which an inlet side occlusion cam 310 is attached, and a tension bar outlet end 316, to which an outlet side occlusion cam 312 is attached. Accordingly, the tension bar 308 extends between the inlet and outlet occlusion cams 310, 312. The pump head cover 252 is attached to the occlusion cams 310, 312 such that the occlusion cams 310, 312 are configured to rotate as the cover 252 pivots between its closed position and open position. As shown in FIGS. 6 and 8-10, the tension bar inlet end 314 extends into the inlet side occlusion cam 310, the tension bar outlet end 316 extends into the outlet side occlusion cam 312, and the pump head cover 252 is secured to each of the occlusion cams 310, 312.

Additionally, the occlusion cams 310, 312 contact the occlusion bed 266. Thus, as the cover 252 pivots from the closed position toward the open position, the occlusion cams 310, 312 rotate, and the cam defined by each of the inlet side occlusion cam 310 and outlet side occlusion cam 312 travels along an upper surface 318 of the occlusion bed 266, applying a force to the occlusion bed 266 to guide the occlusion bed 266 along the one or more guide rails 272 away from the rotor assembly 262 and rotor guide 268. As the cover 252 pivots from the open position toward the closed position, the movement is reversed; the occlusion cams 310, 312 rotate, causing the inlet side occlusion cam 310 and outlet side occlusion cam 312 to travel along the occlusion bed upper surface 318 and apply a force to the occlusion bed 266 to guide the occlusion bed 266 along the one or more guide rails 272 toward the rotor assembly 262 and rotor guide 268. It will be appreciated that the tension bar 308 may determine how easily the occlusion cams 310, 312 rotate as the cover 252 is lifted or lowered, or the amount of force that must be applied by the cams 310, 312 to move the occlusion bed 266; that is, the tension bar 308 maintains the tension on the occlusion cams 310, 312 and, thereby, the occlusion bed 266. As such, the tension bar 308 may allow tuning of the cover opening force, i.e., the tension bar 308 may be adjusted to tighten or loosen the occlusion cams 310, 312, thereby adjusting the amount of force a user must apply to the pump head cover 252 to lift the cover 252 away from or lower the cover 252 toward the pump head 200.

Thus, the pump head 200 is configured to supply a fluid to the cooling circuit 140, which comprises one or more internal lumens for circulating the fluid to the distal end 194 of an energy delivery device 192 of a medical probe assembly 106 for delivering energy to a patient's body. The pump head 200 includes features for defining a tubing pathway 274 through the pump head 200, such that fluid from a fluid source 210 may be urged through tubing 208, which is loaded into the pump head 200 in contact with a rotor assembly 262, and into the cooling circuit 140. Features such as the bezel stop(s) 254, rotor cover plate 296, and closure detection mechanism 302 help prevent misloading of the tubing 208 in the pump head 200, as well as help facilitate user-safe loading of the tubing 208. Further, the pump system 120, pump assembly 122, and pump head 200 described herein are cost effective, easy to use, and robust designs, which may be used as peristaltic pump units for providing cooling fluid to medical probe assemblies, such as probe assemblies 106. Other advantages and benefits of the present subject matter are described or may be ascertained from the discussion herein.

A system of the present subject matter may be used in various medical procedures where usage of an energy delivery device may prove beneficial. Specifically, the system of the present subject matter is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probe assemblies 106 with an appropriate feedback control system as described herein also contributes to the uniformity of the treatment. The cooling distal tip regions 190 of the probe assemblies 106 helps to prevent excessively high temperatures in these regions which may lead to tissue adhering to the probe assemblies 106 as well as an increase in the impedance of tissue surrounding the distal tip regions 190 of the probe assemblies 106. Thus, by cooling the distal tip regions 190 of the probe assemblies 106, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

As has been mentioned, a system of the present subject matter may be used to produce a relatively uniform lesion substantially between two probe assemblies 106 when operated in a bipolar mode. Oftentimes, uniform lesions may be contraindicated, such as in a case where a tissue to be treated is located closer to one energy delivery device 192 than to the other. In cases where a uniform lesion may be undesirable, using two or more cooled probe assemblies 106 in combination with a suitable feedback and control system may allow for the creation of lesions of varying size and shape. For example, preset temperature and/or power profiles that the procedure should follow may be programmed into the generator 102 prior to commencement of a treatment procedure. These profiles may define parameters (these parameters would depend on certain tissue parameters, such as heat capacity, etc.) that should be used to create a lesion of a specific size and shape. These parameters may include, but are not limited to, maximum allowable temperature, ramp rate (i.e. how quickly the temperature is raised) and the rate of cooling flow, for each individual probe. Based on temperature or impedance measurements performed during the procedure, various parameters, such as power or cooling, may be modulated, to comply with the preset profiles, resulting in a lesion with the desired dimensions.

Similarly, it is to be understood that a uniform lesion can be created, using a system of the present subject matter, using many different pre-set temperature and/or power profiles which allow the thermal dose across the tissue to be as uniform as possible, and that the present subject matter is not limited in this regard.

It should be noted that the term radiopaque marker as used herein denotes any addition or reduction of material that increases or reduces the radiopacity of the device. Further, the terms probe assembly, introducer, stylet etc. are not intended to be limiting and denote any medical and surgical tools that can be used to perform similar functions to those described. In addition, the subject matter is not limited to be used in the clinical applications disclosed herein, and other medical and surgical procedures wherein a device of the present subject matter would be useful are included within the scope of the present subject matter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A pump head for a peristaltic pump, comprising:
   an occlusion bed;
   a rotor guide;
   a rotor assembly positioned between the occlusion bed and the rotor guide; and wherein the rotor guide defines a rotor guide recess for the rotor assembly, and
   a pathway for tubing, the pathway comprising an inlet portion, an outlet portion, and a connecting portion that connects the inlet portion to the outlet portion,
   wherein the rotor guide has a rotor guide inlet side defining a rotor guide inlet groove and a rotor guide outlet side defining a rotor guide outlet groove,
   wherein the occlusion bed is movable with respect to the rotor guide and the rotor assembly,
   wherein the inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly,
   wherein the occlusion bed has an occlusion bed inlet side and an occlusion bed outlet side, the occlusion bed outlet side defining a slot for the tubing, the slot tapering from the occlusion bed outlet side toward a midline of the pump head,
   wherein the tubing is compressed between the occlusion bed inlet side and the rotor guide inlet groove, and
   wherein the tubing is seated on the rotor guide outlet groove and is free to slide into the slot.

2. The pump head of claim 1, wherein the rotor assembly comprises:
   a mounting block;
   a plurality of roller bearings; and
   a cover plate,
   wherein a rotor of a motor is positioned in operative communication with the mounting block to drive the rotor assembly.

3. The pump head of claim 2, wherein the connecting portion of the pathway is defined between the rotor assembly and the occlusion bed such that the tubing contacts at least one roller bearing of the plurality of roller bearings.

4. The pump head of claim 2, wherein the cover plate defines a gap between the rotor assembly and the occlusion bed for receipt of the tubing.

5. The pump head of claim 1, further comprising:
   a cover having a closed position and an open position; and
   a mounting plate,
   wherein the cover pivots with respect to the mounting plate to alternate between the closed position and the open position.

6. The pump head of claim 5, wherein the occlusion bed, rotor guide, rotor assembly, and pathway are disposed between the cover and the mounting plate such that the pathway is inaccessible by a user of the pump head when the cover is in the closed position and the pathway is accessible by the user when the cover is in the open position.

7. The pump head of claim 6, wherein the cover extends adjacent the rotor guide, and
   wherein the rotor guide defines a depression to provide finger space for the user to open the cover.

8. The pump head of claim 5, wherein the mounting plate comprises an upper portion and an opposite lower portion, the lower portion defining an opening for fluid to flow away from the pump head.

9. The pump head of claim 5, further comprising:
   a closure detection mechanism including a first element and a second element,
   wherein the first element is positioned on the cover and the second element is positioned on the mounting plate such that a circuit is closed when the cover is in the closed position and is open when the cover is in the open position, and
   wherein the circuit controls a motor of the rotor assembly such that the motor is operable when the circuit is closed and is inoperable when the circuit is open.

10. The pump head of claim 5, further comprising:
    an inlet side occlusion cam; and
    an outlet side occlusion cam,
    wherein the cover is attached to both the inlet side occlusion cam and the outlet side occlusion cam such that the inlet and outlet side occlusion cams are configured to rotate as the cover pivots between the closed position and the open position, and
    wherein the inlet side occlusion cam and the outlet side occlusion cam each contact the occlusion bed to move the occlusion bed with respect to the rotor guide as each of the inlet side occlusion cam and outlet side occlusion cam rotate.

11. The pump head of claim 10, further comprising:
    a tension bar having a tension bar inlet end and a tension bar outlet end,
    wherein the inlet side occlusion cam is attached to the tension bar inlet end and the outlet side occlusion cam is attached to the tension bar outlet end such that the tension bar extends between the inlet side and outlet side occlusion cams.

12. The pump head of claim 1, further comprising:
a guide rail,
wherein the occlusion bed is received on the guide rail such that the guide rail guides the occlusion bed as the occlusion bed moves with respect to the rotor guide.

13. The pump head of claim 1, wherein the pump head is configured to supply a fluid to a cooling circuit, the cooling circuit comprising one or more internal lumens for circulating the fluid to a distal end of an energy delivery device of a probe of a medical probe assembly for delivering energy to a patient's body.

14. A pump head for a peristaltic pump, comprising:
a mounting plate;
an occlusion bed;
a rotor guide;
a rotor assembly positioned between the occlusion bed and the rotor guide; wherein the rotor guide defines a rotor guide recess for the rotor assembly;
a pathway for tubing, the pathway comprising an inlet portion, an outlet portion, and a connecting portion that connects the inlet portion to the outlet portion; and
a cover having a closed position and an open position,
wherein the occlusion bed, rotor guide, rotor assembly, and pathway are disposed between the mounting plate and the cover,
wherein the cover pivots between the closed position and the open position to selectively expose the occlusion bed, rotor guide, rotor assembly, and pathway,
wherein the rotor guide has a rotor guide inlet side defining a rotor guide inlet groove and a rotor guide outlet side defining a rotor guide outlet groove,
wherein the occlusion bed is configured to move away from the rotor guide as the cover pivots from the closed position to the open position and the occlusion bed is configured to move toward the rotor guide as the cover pivots from the open position to the closed position,
wherein the occlusion bed has an occlusion bed inlet side and an occlusion bed outlet side, the occlusion bed outlet side defining a slot for the tubing, the slot tapering from the occlusion bed outlet side toward a midline of the pump head,
wherein the tubing is compressed between the occlusion bed inlet side and the rotor guide inlet groove when the cover is in the closed position, and
wherein the tubing is seated on the rotor guide outlet groove and is free to slide into the slot.

15. The pump head of claim 14, wherein the inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly.

16. The pump head of claim 14, wherein the pathway has a width when the cover is in the open position, and
wherein the width of the pathway is determined by an angle between the cover and the pump head.

17. A pump head for a peristaltic pump, comprising:
an occlusion bed;
a rotor guide;
a rotor assembly positioned between the occlusion bed and the rotor guide, the occlusion bed defining an occlusion bed recess for the rotor assembly and the rotor guide defining a rotor guide recess for the rotor assembly, the rotor assembly configured to rotate with respect to the occlusion bed and the rotor guide; and
a pathway for tubing, the pathway comprising an inlet portion, an outlet portion, and a connecting portion that connects the inlet portion to the outlet portion,
wherein the occlusion bed is movable with respect to the rotor guide and the rotor assembly,
wherein the inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly,
wherein the rotor guide has a rotor guide inlet side defining a rotor guide inlet groove and a rotor guide outlet side defining a rotor guide outlet groove,
wherein the occlusion bed has an occlusion bed inlet side and an occlusion bed outlet side, the occlusion bed outlet side defining a slot for the tubing, the slot tapering from the occlusion bed outlet side toward a midline of the pump head,
wherein the tubing is compressed between the occlusion bed inlet side and the rotor guide inlet groove,
wherein the tubing is seated on the rotor guide outlet groove and is free to slide into the slot, and
wherein the pump head urges fluid flow through the tubing to supply a cooling fluid to a medical probe assembly for delivering energy to a patient's body, the medical probe assembly comprising:
at least one probe having an elongate member with a distal region and a proximal region, the distal region comprising an electrically non-conductive outer circumferential portion, and
an electrically and thermally-conductive energy delivery device extending distally from the electrically non-conductive outer circumferential portion for delivering one of electrical and radiofrequency energy to the patient's body, the energy delivery device comprising a conductive outer circumferential surface and one or more internal lumens for circulating the cooling fluid to a distal end of the energy delivery device.

18. A pump head for a peristaltic pump, comprising:
a mounting plate;
an occlusion bed;
a rotor guide;
a rotor assembly positioned between the occlusion bed and the rotor guide;
a pathway for tubing, the pathway comprising an inlet portion, an outlet portion, and a connecting portion that connects the inlet portion to the outlet portion; and
a cover having a closed position and an open position,
wherein the occlusion bed, rotor guide, rotor assembly, and pathway are disposed between the mounting plate and the cover,
wherein the cover pivots between the closed position and the open position to selectively expose the occlusion bed, rotor guide, rotor assembly, and pathway,
the occlusion bed has an occlusion bed inlet side and an occlusion bed outlet side, the occlusion bed outlet side defining a slot for the tubing, the slot tapering from the occlusion bed outlet side toward a midline of the pump head,
wherein the rotor guide has a rotor guide inlet side defining a rotor guide inlet groove and a rotor guide outlet side defining a rotor guide outlet groove,
wherein the tubing is compressed between the occlusion bed inlet side and the rotor guide inlet groove, and wherein the tubing is seated on the rotor guide outlet groove and is free to slide into the slot; and wherein the occlusion bed is configured to move away from the rotor guide as the cover pivots from the closed position to the open position and the occlusion bed is configured to move toward the rotor guide as the cover pivots from the open position to the closed position.

\* \* \* \* \*